United States Patent
Sterman et al.

(10) Patent No.: US 6,699,231 B1
(45) Date of Patent: Mar. 2, 2004

(54) METHODS AND APPARATUS FOR PERFUSION OF ISOLATED TISSUE STRUCTURE

(75) Inventors: Wesley D. Sterman, San Francisco, CA (US); John H. Stevens, Palo Alto, CA (US); Hanson S. Gifford, III, Woodside, CA (US); Lawrence C. Siegel, Hillsborough, CA (US); Joe B. Putnam, Houston, TX (US)

(73) Assignee: Heartport, Inc., Redwood City, CA (US)

( * ) Notice: Subject to any disclaimer, the term of this patent is extended or adjusted under 35 U.S.C. 154(b) by 0 days.

(21) Appl. No.: 09/223,229

(22) Filed: Dec. 30, 1998

Related U.S. Application Data
(60) Provisional application No. 60/070,087, filed on Dec. 31, 1997.

(51) Int. Cl.[7] ............ A61M 31/00; A61M 37/00; A61M 29/00
(52) U.S. Cl. ............ 604/509; 604/4.01; 604/507; 604/508; 604/93.01; 604/96.01; 604/6.14
(58) Field of Search .................. 604/500, 507, 604/508, 509, 6.14, 5.01, 4.01, 6.16, 8, 6.11, 93.01, 96.01, 264; 606/27–31; 128/DIG. 3; 435/1.1, 1.2, 284.1; 210/758; 422/44, 45; 261/19

(56) References Cited

U.S. PATENT DOCUMENTS

| | | | |
|---|---|---|---|
| 4,192,302 A | | 3/1980 | Boddie |
| 4,345,588 A | | 8/1982 | Widder et al. |
| 4,540,402 A | | 9/1985 | Aigner |
| 4,563,170 A | | 1/1986 | Aigner |
| 4,648,865 A | | 3/1987 | Aigner |
| 4,666,425 A | * | 5/1987 | Fleming ............ 128/897 |
| 4,666,426 A | | 5/1987 | Aigner |
| 4,714,460 A | | 12/1987 | Calderon |
| 4,820,261 A | | 4/1989 | Schmoll et al. |
| 4,867,742 A | | 9/1989 | Calderon |
| 4,883,459 A | | 11/1989 | Calderon |
| 5,007,897 A | | 4/1991 | Kalb et al. |
| 5,069,662 A | | 12/1991 | Bodden |
| 5,087,244 A | | 2/1992 | Wolinsky et al. |
| 5,135,474 A | | 8/1992 | Swan et al. |
| 5,158,536 A | | 10/1992 | Sekins et al. |

(List continued on next page.)

FOREIGN PATENT DOCUMENTS
WO     WO 94/22519     10/1994

OTHER PUBLICATIONS

Brown, Henry and Hardison, W.G. "Flourocarbon sonicated as a substitute for erythrocytes in rat liver perfusion". Surgery, Mar. 1972, 71, 3, 388–394.*

Fujimura et al., "Intrathoracic hyperthermochemotherapeutic perfusion for the intrathoracic malignancies in gastric cancer" Hepato–Gastroenterology (1995) 42:878–884.

Johnston et al., "Isolated lung perfusion with Andriamycin" Cancer (1983) 52:404–409.

(List continued on next page.)

*Primary Examiner*—Brian L. Casler
*Assistant Examiner*—Catherine S. Williams

(57) ABSTRACT

Organs and other tissue structures are isolated and perfused with a therapeutic agent. Isolation is effected by endovascularly positioning catheters having occlusion balloons within the arteries or other blood vessels which supply blood to the organ. Similarly, blood flow from the organ back to the patient's circulatory system is blocked by endovascularly positioning one or more catheters carrying occlusion members within the veins or other blood vessels leading from the organ. The therapeutic agent may then be perfused through the organ in either an antegrade or retrograde fashion using the endovascularly positioned catheters while maintaining isolation.

18 Claims, 27 Drawing Sheets

U.S. PATENT DOCUMENTS

| | | | |
|---|---|---|---|
| 5,163,905 | A | 11/1992 | Don Michael |
| 5,167,628 | A | 12/1992 | Boyles |
| 5,209,717 | A | 5/1993 | Schmoll et al. |
| 5,328,470 | A | 7/1994 | Nabel et al. |
| 5,411,479 | A | 5/1995 | Bodden |
| 5,451,207 | A * | 9/1995 | Yock .................. 604/19 |
| 5,458,574 | A | 10/1995 | Machold et al. |
| 5,478,309 | A * | 12/1995 | Sweezer et al. |
| 5,505,700 | A | 4/1996 | Leone et al. |
| 5,556,389 | A | 9/1996 | Liprie |
| 5,599,307 | A | 2/1997 | Bacher et al. |
| 5,716,410 | A * | 2/1998 | Wang et al. |
| 5,730,720 | A * | 3/1998 | Sites et al. |
| 5,746,717 | A | 5/1998 | Aigner |
| 5,766,901 | A | 6/1998 | Mann et al. |
| 5,817,046 | A * | 10/1998 | Glickman .............. 604/5.04 |
| 5,922,687 | A | 7/1999 | Mann et al. |
| 6,071,271 | A * | 6/2000 | Baker et al. |
| 6,077,256 | A * | 6/2000 | Mann .................. 604/173 |
| 6,287,273 | B1 * | 9/2001 | Allers et al. .............. 604/27 |

OTHER PUBLICATIONS

Matsuzaki et al., "Intrapleural perfusion hyperthermo– chemotherapy for malignant pleural dissemination and effusion" Ann. Thorac. Surg. (1994) 59:127–131.

Minchin et al. "Pharmacokinetics of Doxorubicin in isolated lungs for dogs and humans perfused in vivo" J. Pharmacol. Exp. Therap. (1984) 229:193–198.

Progrebniak et al., "Isolated lung perfusion with tumor necrosis factor: A swine model in preparation of human trials" Ann. Thorac. Surg. (1994) 57:1477–1483.

Turrisi, "Innovations in multimodality for lung cancer" Chest (1993) 103:565–595.

Wang et al., "Prospective trial of combined hyperfractionated radiotherapy and bronchial arterial infusion of chemotherapy for locally advanced nonsmall cell lung cancer" Int. J. Radiation Oncology Biol. Phys. (1996) 34:309–311.

Wantanabe et al., "Reappraisal of bronchial arterial infusion therapy for advanced lung cancer" Jpn. J. Surg. (1990) 20:27–35.

Abolhoda et al., "Isolated lung perfusion with doxorubicin prolongs survival in rodent model pulmonary metastases" Ann. Thorac. Surg. (1997) 64:181:184.

Fried et al., "Safe, compact and portable system for regional chemotherapeutic perfusion procedures" J. Extra–Corpor. Tech. (1993) 25:22–26.

* cited by examiner

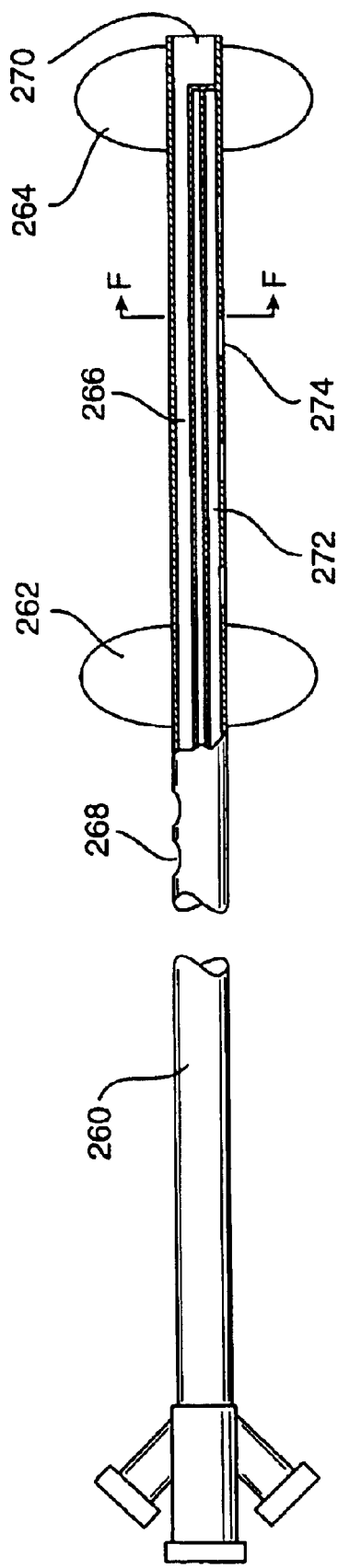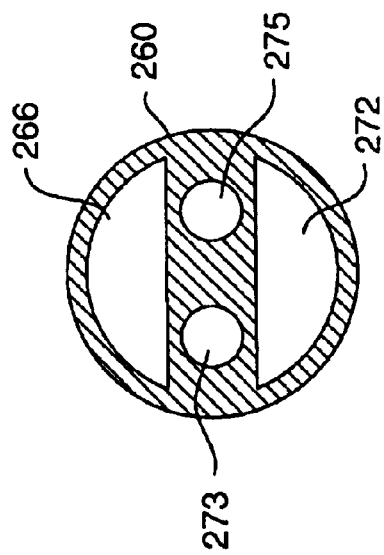
FIG. 6E
FIG. 6F

METHODS AND APPARATUS FOR PERFUSION OF ISOLATED TISSUE STRUCTURE

CROSS-REFERENCE TO RELATED APPLICATIONS

This application claims priority from co-pending provisional application serial No. 60/070,087, filed Dec. 31, 1997.

BACKGROUND OF THE INVENTION

1. Field of the Invention

The present invention relates generally to the localized delivery of therapy to specific tissue structures in a patient. More particularly, the present invention relates to methods and apparatus for delivering therapeutic and diagnostic agents and other forms of therapy to a tissue structure while the tissue structure is isolated from systemic circulation.

Systemic chemotherapy for the treatment of cancer and other diseases can be effective, but suffers from a number of undesirable side-effects. Many chemotherapeutic agents are cytotoxic with selectivity for rapidly dividing neoplastic (cancerous) cells. It is desirable to use relatively high dosages of these agents in order to approach or achieve complete eradication of the cancerous cells. Such high dosages, however, can have a very harsh impact on the patient, including bone marrow toxicity, hair loss, nausea, fever, inability to digest food, and even death.

To lessen such systemic toxicity, isolated perfusion of organs and limbs with chemotherapeutic agents has been proposed. For example, limbs have been isolated from circulation using an externally applied tourniquet while an artificial blood circulation is maintained within the limb as the chemotherapeutic agent is administered. In another example, the liver has been isolated on the systemic venous side using a balloon catheter while a chemotherapeutic agent is injected into the liver. In a third example, a very complex shunt system has been surgically implanted for isolating the liver and recirculating oxygenated blood carrying a chemotherapeutic agent, as described in U.S. Pat. No. 4,192,302. Known methods, however, have not enabled complete isolation of an organ to eliminate the risks of systemic toxicity, with the ability to maintain localized circulation through the organ as well as systemic circulation to the remainder of the organism, by means of devices positioned solely through endovascular or less-invasive surgical access. Therefore, such methods have not gained wide acceptance for chemotherapy or other diagnostic and therapeutic procedures.

It would therefore be desirable to provide improved methods, systems, apparatus, and kits for the localized delivery of therapeutic agents, diagnostic agents, and other forms of therapy to organs and other tissue structures for the treatment and diagnosis of cancers and other diseases. Preferably, such systems will provide complete or substantially complete isolation of the organ or tissue structure. Both isolation and perfusion will preferably be achieved without major surgical incisions, more preferably via minimally invasive access routes, and most preferably via an endovascular access route through a peripheral or other connecting blood vessel to arteries or veins associated with the tissue structure. Isolation of the tissue structure should permit both total recirculation of blood or other oxygenated carrier within the tissue to be treated and alternatively once-through perfusion of the tissue. In all cases, it will preferably be possible to achieve tissue perfusion in either an antegrade, retrograde, or combination antegrade/retrograde manner. The present invention will meet these and other objectives.

2. Description of the Background Art

A shunt system for circulating a chemotherapeutic agent through the liver in an open surgical procedure is described in U.S. Pat. No. 4,192,302. Catheters and systems for the localized delivery of chemotherapeutic and other therapeutic agents are described in U.S. Pat. Nos. 5,411,479; 5,209,717; 5,135,474; 5,069,662; 4,883,459; 4,867,742; 4,820,261; 4,714,460; 4,345,588; and PCT Application WO 94/22519. Intravascular and other drug delivery catheters are described in U.S. Pat. Nos. 5,599,307; 5,556,389; 5,505,700; 5,328,470; 5,167,628; 5,163,905; 5,087,244; 5,007,897; and 4,540,402. Intravascular bypass catheter systems are described in U.S. Pat. Nos. 5,478,309; 5,458,574; and 5,451,207. A catheter for hyperthermic treatment of a lung malignancy employing a perfluorocarbon medium is described in U.S. Pat. No. 5,158,536. Isolated organ and limb perfusion is discussed in Wang et al. (1996) Int. J. Radiation Oncology Biol. Phys. 34:309–311; Fajimura et al. (1995) Hepato-Gastroenterology 42:878–884; Matsuzaki et al. (1995) Ann. Thorac. Surg. 59:127–131; Pogrebniak et al. (1994) Ann. Thorac. Surg. 57:1477–1483; Turrisi 91993) Chest 103:565–595; Fried et al. (1993) J. Extra-Corpor. Tech. 25:22–26; Watanabe et al. (1990) Jpn. J. Surg. 20:27–35; Minchin et al. (1984) J. Pharmacol. Exp. Therap. 229:193–198; and Johnston et al. (1983) Cancer 52:404–409.

SUMMARY OF THE INVENTION

The present invention provides improved methods, systems, apparatus, and kits for the isolated perfusion of organs and other tissue structures. The systems, including multiple catheters as described in more detail below, can provide for partial or complete isolation of the vasculature of a tissue structure from the remainder of the patient's circulatory system. By providing such isolation, the vasculature within the tissue structure may be perfused with a desired therapeutic or diagnostic agent, with added or varied concentrations of oxygen, typically via recirculation of blood or other oxygen-carrying medium through the vasculature of the tissue structure with minimum or no loss of the agent into systemic circulation. Perfusion and/or recirculation may be achieved in an antegrade direction, a retrograde direction, or some combination of antegrade and retrograde directions. Additionally, various parameters within the isolated organ, such as temperature, pressure, chemical concentrations, and vascular permeability, may be adjusted for maximum local effect without systemic effect. Thus, the apparatus and methods of the invention enable the perfusion of organs and other tissue structures with therapeutic agents which are currently unavailable for systemic delivery due to their toxicity, as well as perfusion with currently-utilized therapeutic agents, but at such dosage levels, pressures, and temperatures or under such other conditions that systemic delivery would be harmful.

Methods according to the present invention preferably rely on first isolating the tissue structure from the patient's circulatory system and then delivering a therapeutic agent to the tissue structure. The tissue structure is isolated by endovascularly positioning a first catheter in an artery which supplies blood to the tissue structure and, preferably, deploying a first occluding member on or over the catheter to occlude the artery. A second catheter is endovascularly positioned in a vein to which blood drains from the tissue structure and deploying a second occluding member on or over the second catheter to occlude the vein. The therapeutic or diagnostic agent is then perfused through the vasculature of the tissue structure via at least one of the first and second catheters, while blood circulation continues through the remainder of the patient circulatory system and the vasculature of the tissue structure remains isolated from the circulatory system. In some cases it may not be necessary to occlude the artery supplying blood to the target organ, since the direction of blood flow into the organ will inhibit leakage of the therapeutic agent into the remainder of the arterial system. However, in most cases occlusion of both the arteries supplying blood to the organ and veins draining blood from the organ will be preferred so as to enable total isolation and perfusion of the organ without risk of systemic effects. As used herein, the term "isolating" may be used to mean complete isolation of an organ, by occluding all arteries supplying blood to the organ and all veins draining blood from the organ, or for partial isolation of the organ, wherein only some of such arteries and/or veins are occluded. Thus, the invention may be used to reduce normal circulation through the organ by, for example, as little as 30%–50%, preferably by 60%–80%, and most preferably by as much as 100%.

Usually, only those blood vessels which supply blood to the organ or other tissue structure for maintaining viability of that tissue will be isolated. That is, blood vessels which supply blood to an organ for processing by the organ will usually remain patent. In some instances, however, it may be desirable to also occlude those blood vessels which supply and drain blood from an organ for processing as well. Additionally, in some cases the methods of the invention may involve occlusion of other fluid vessels communicating with an organ, such as lymph ducts, bile ducts, the airways of the lungs, the urinary tract, or digestive tract. By "endovascularly positioning," it is meant that the catheters are introduced through a remote blood vessel or other type of vessel, usually a peripheral blood vessel, and guided to the target artery or vein intravascularly, typically over a guidewire or by other conventional intravascular placement techniques.

The occluding member(s) will typically be positioned on the catheter at a location which permits deployment when a port or other passage on the catheter is located within the target artery or vein at a desired position. Alternatively, the occluding members may be deployed in a larger artery or vein from which the target artery or vein branches. In this case, a pair of spaced-apart occluding members may be utilized on the catheter to occlude the larger artery or vein on either side of the branching target vessel. The occluding member is preferably an inflatable balloon, but it could also be a variety of other deployable elements, such as flanges, umbrellas, collapsible valves, flapper valves, pivoting disk valves, expandable coated mesh elements, or the like. The occluding member could also be deployed separately from the catheter, such as an externally deployed clamp or snare which may be placed over a blood vessel to externally seal the blood vessel against the catheter. Such external clamps could be placed using an open surgical technique, but would more usually be placed using minimally invasive techniques employing cannulae or trocar sleeves and indirect vision, e.g. an endoscope and associated video display.

The catheters and methods of the invention may also be used to isolate portions of an organ for even more specific isolation and perfusion of therapeutic agent. Additionally, for bilateral organs having bilateral (right and left) arterial supply and venous drainage systems such as the lungs, kidneys, prostate, stomach, ovaries, and testicles, the methods of the invention may be used for either unilateral or bilateral isolation and perfusion by subselecting the vessels on the right side, left side or both for occlusion and perfusion. Further, it may be desirable in some instances to perfuse the organ unilaterally and collect the agent bilaterally, in the event of any communication between the vasculature of the two sides.

Preferably, the methods of the present invention further comprise collecting the therapeutic agent through at least one of the first and second catheters while the tissue structure remains isolated and the perfusate continues to be delivered. In this way, a complete perfusion of the vasculature of the tissue structure can be achieved. Optionally, the therapeutic agent may be delivered through more than one catheter and/or collected through more than one catheter in order to enhance both the rate and completeness of the perfusion. By delivering the perfusate through the first catheter into the arterial side of the tissue structure and collecting the agent through the second catheter on the venous side of the tissue structure, antegrade perfusion can be established. Conversely, by delivering the therapeutic agent through the second catheter on the venous side of the tissue structure and collecting the therapeutic agent through the first catheter on the arterial side, retrograde perfusion can be established. In some instances, when more than two catheters are utilized, combinations of antegrade and retrograde perfusion can be performed simultaneously or sequentially.

As a further alternative method, perfusate may be delivered by either the first or second catheter individually, and collected by the same catheter by applying negative pressure through its lumen. Preferably, the perfusate is allowed to dwell in the organ for a period of time to maximize therapeutic effect, during which time the balloon on the delivery catheter prevents blood from flushing the perfusate from the organ. In this way, a single catheter may be used to isolate and perfuse all or a portion of an organ.

The tissue structure will usually be an organ, preferably being selected from the group consisting of the brain, lungs, breast, kidneys, liver, spleen, stomach, small and large bowel, pancreas, colon, bladder, thyroid gland, uterus, prostate, testicles, ovaries, and the like. The perfusate may comprise a variety of active agents, including therapeutic agents, diagnostic agents, sensitizing agents, potentiating agents and combinations thereof. Exemplary diagnostic agents include radio nucleotides, labelled antibodies, dyes, contrast media, and other diagnostic materials of the type which are generally delivered systemically but which could benefit from isolated organ-specific or tissue-specific delivery. Useful therapeutic agents include drugs, biologic materials, and the like. Exemplary chemotherapeutic drugs include adriamycin, methotrexate, taxol, bleomycin, and the like. Biologic treatments include antibodies, nucleic acids (for gene therapy), proteins, cellular materials, growth factors, and the like. In particular, the methods and systems of the present invention may be usual for performing cellular transplantation. For example, in a patient whose liver has been damaged by chemotherapy or other causes, it will be possible to infuse hepatic cells back into the isolated liver, typically with growth factors, nutrients, and the like, in order to promote regeneration of the liver.

In addition, the methods of the invention may be used to regulate various other parameters of blood or fluids in an organ including temperature, hydrostatic pressure, osmotic or oncotic pressure and regional fluid volume within the organ. Such parameters may be altered to control or enhance uptake or effectiveness of a particular drug, sensitizing or potentiating agent, dye or marker, to facilitate visualization of the organ (using X-ray, magnetic resonance imaging, light or ultrasound), or to otherwise alter biochemical processes within the organ. Further, the oxygen concentration within the blood or fluid in the organ may be varied for enhanced therapeutic effect. In some cases, the effectiveness of a particular drug may be enhanced by delivering it with an oxygen rich fluid, while with other drugs, a hypoxic environment may be created to enhance a drug's effectiveness.

In a preferred aspect of the method, the delivering step will comprise delivering both the therapeutic agent and an oxygenated vehicle or carrier to the tissue structure. It will be appreciated that isolation of the tissue structure from a patient's circulation may deprive the tissue structure of blood and oxygen. While oxygen deprivation will not always be a problem, in at least some instances provision of oxygen to the tissue structure can permit significant lengthening of the treatment protocol. Without continuing oxygenation of the tissue structure, treatment will in some cases be limited to a period of time less than 60 minutes, usually less than 30 minutes, depending upon the particular organ being treated. By delivering the therapeutic agent together with an oxygenated vehicle, the treatment times can be extended significantly, typically to a period longer than 60 minutes, often to a period longer than two hours, and sometimes for a period of four hours, or longer. Treatment periods may be even longer if the target organ and/or the entire organism is cooled during treatment. Thus, the invention enables significantly longer periods of treatment or diagnosis than can be tolerated with systemic administration of toxic agents. However, in the case of some drugs, therapeutic effect may be enhanced by inducing hypoxia in the target tissue. Thus, in some cases, delivery of the therapeutic agent in an oxygen-depleted medium will be preferred.

The oxygenated vehicle may comprise a synthetic oxygen carrier, such as a perfluorocarbon or other blood substitute material. More usually, however, the oxygenated vehicle will be oxygenated blood, typically blood withdrawn and recirculated from the patient being treated. In particularly preferred protocols, blood will be obtained from the patient, combined with a therapeutic and/or diagnostic agent, and the resulting combination perfused through the catheter(s) into and through the tissue structure. Most preferably, the perfused blood, synthetic oxygen carrier, or combination of blood and synthetic carrier will then be collected through one or more of the other catheters, reoxygenated, usually filtered, and returned to the vasculature of the tissue structure, typically in a recirculating manner. Optionally, the blood and/or synthetic oxygen carrier could be superoxygenated. While less preferred, it will also be possible to recirculate and reoxygenate synthetic oxygen carriers. It will also be possible to utilize both the synthetic oxygen carriers and patient (autologous) or heterologous blood in a once-through manner, where the vehicle is collected and then disposed.

In a most preferred aspect, the therapeutic agent delivering step comprises establishing extracorporeal recirculation through the vasculature of the isolated tissue structure. In particular, the establishing step comprises delivering a medium comprising the therapeutic agent and blood or other oxygen carrier through one of the catheters. The medium is then collected through another of the catheters after the medium has perfused at least a portion of the tissue structure. The collected medium is then extracorporeally pumped back through the first catheter after it has been oxygenated. Usually, the medium is filtered after it is collected and before it is returned to the patient. Optionally, therapeutic agent will be continuously or intermittently introduced to the medium as it is being extracorporeally recirculated.

In another aspect of the present invention, a medium of the therapeutic agent and an oxygen carrier may be provided, typically in a relatively large volume. The medium may then be delivered to the tissue structure through one of the catheters and collected after it has perfused the tissue structure from another of the catheters. Optionally, the medium may be allowed to dwell in the organ for a desired period of time before collection to optimize therapeutic effect. The medium will not be recirculated.

An additional method of treatment of a tissue structure according to the invention comprises endovascularly occluding an artery and a vein and endovascularly delivering a therapeutic agent to the tissue structure at a systemically toxic concentration or dose, the systemically toxic concentration or dose being substantially greater than, usually at least 1.5 times, frequently at least 2 to 10 times, and preferably up to 100 times the concentration or dose clinically acceptable for systemic delivery. As used herein the term "clinically acceptable for systemic delivery" means that concentration or dose of the therapeutic agent which is approved by the US Food and Drug Administration or other relevant regulatory body, or if such approval is not applicable to such therapeutic agent, the concentration or dose which is recommended by the manufacturer of such therapeutic agent, or in the absence of such recommendation, then the concentration or dose which is generally accepted for systemic delivery without isolation of the target organ according to currently published literature in the relevant field. In this way, the invention enables therapeutics to be delivered to an isolated organ which are too toxic for systemic delivery. The optimal dose delivered will be determined by a number of factors, including the degree of response in the tumor, necrosis or injury to healthy tissue in the target organ, immunologic responses and the creation of other adverse effects. Moreover, the invention enables therapeutic agents to be delivered at the dosage levels currently used for systemic administration, but with greatly reduced or eliminated adverse systemic effects.

Still another method of treatment of a tissue structure comprises delivering a therapeutic agent to the tissue structure; and heating the tissue structure during the delivering step so as to increase cellular uptake or efficacy of the therapeutic agent. During delivery or recirculation of the therapeutic agent, an organ may be heated to a temperature in excess of normal body temperature (98.6° F.) to a point higher than what might be tolerated systemically, e.g. higher than 100° F., preferably 101–105° F., more preferably 106–110° F., and in some cases 110–120° F. Usually the organ will be heated by first heating the therapeutic agent before it is delivered such that heat is transferred from the therapeutic agent to the organ upon delivery. Additionally, it may be desirable to utilize heating and cooling to create temperature differences between various structures so as to enhance the selectivity of the therapeutic agent. For example, certain organs targeted for therapy may be heated to enhance efficacy of the agent delivered, while other organs are cooled to inhibit the therapeutic effect of the agent in such organs. Further, heating or cooling an isolated organ may have therapeutic effects even without delivering any therapeutic agent. This may be accomplished by delivering or recirculating heated or cooled saline or other suitable fluid through the organ using the catheters and methods described herein to raise or lower the organ temperature for a desired time period.

In a first exemplary method according to the present invention, the tissue structure is a lung, the first catheter occludes a pulmonary artery, the second catheter occludes a superior pulmonary vein, and a third catheter occludes an inferior pulmonary vein. Alternatively, or additionally, the method may further comprise occluding the pulmonary venous ostia in the left atrium, individually or together by means of a diaphragm extending around both ostia. The second and third catheters may be introduced from the venous side via a transseptal puncture, or from the arterial side via the aorta, aortic valve and mitral valve. The therapeutic agent may be delivered through the first catheter and collected in at least one of the second and third catheters to establish antegrade perfusion. Alternatively, the therapeutic agent may be delivered through at least one of the second and third catheters and collected in the first catheter to establish retrograde perfusion. In another alternative method, only the first catheter is used and the therapeutic agent is delivered into the pulmonary artery, allowed to dwell in the lungs while the first balloon occludes the pulmonary artery to prevent flushing, then collected through the first catheter. Similarly, only the second and third catheters may be used to deliver the therapeutic agent in a retrograde manner into the pulmonary veins, and the same two catheters used to collect the agent from the pulmonary veins. Additionally, the first catheter may have at least two balloons at spaced apart locations near the catheter's distal end to facilitate occlusion of the pulmonary artery on opposing sides of one or more branching arteries, thereby allowing selective perfusion of particular regions of the lung.

The method of isolated perfusion of the lung may be further enhanced by concurrent delivery of a therapeutic agent, sensitizing agent, potentiating agent, bronchial blocker, steam, solvent, or other suitable substance into the airways of the lung via the bronchus. For example, vasomotor tone may be modified by altering the gas mixture in the lung, thereby altering local pulmonary circulation and enhancing selectivity of the therapeutic agent to the target lung tissues. Selective ventilation of the lung may also be used to induce hypoxia in selected regions, thereby stimulating pulmonary vasoconstriction in such regions so as to reduce uptake of the therapeutic agent delivered via the pulmonary artery. Vasodilating agents or vasoconstricting agents may be delivered into selected regions of the lungs to alter pulmonary vasoconstriction. Hot or cold fluids may also be introduced to alter vasoconstriction or other parameters. Thus, the method of the invention may further include positioning a delivery tube into a bronchus via the trachea and delivering a therapeutic, diagnostic, sensitizing, or potentiating agent, and/or air, oxygen, carbon dioxide or other fluids, into the lung through the delivery tube. The delivery tube may include an occluding member (e.g. balloon) for occluding the bronchus to maintain the therapeutic agent in the lung. The delivery tube and occluding member may further be positionable in selected branches of the bronchial tree to allow for subselection of a particular region of the lung. The agent may be evacuated from the lung by applying negative pressure to the delivery tube.

In a second exemplary method according to the present invention, the tissue structure is a liver, the first catheter occludes a hepatic artery, the second catheter occludes a hepatic vein, and a third catheter occludes a portal vein. The therapeutic agent may be delivered through at least one of the first and third catheters and collected in the second catheter to establish antegrade perfusion. Alternatively, the therapeutic agent may be delivered through the second catheter and collected in at least one of the first and third catheters to establish retrograde perfusion. The portal vein is preferably catheterized by introducing the third catheter through a transhepatic puncture into the portal vein or branch thereof within the liver. The third catheter may be introduced into the liver either endovascularly from the inferior vena cava and a hepatic vein, or transabdominally from an abdominal incision directly into the liver.

In a third exemplary method according to the present invention, the tissue structure is a brain, the first catheter occludes an internal carotid artery, a third catheter occludes another internal carotid artery, the second catheter occludes an internal jugular vein, and a fourth catheter occludes another internal jugular vein. By occluding these arteries and veins, an anterior segment of the brain is isolated from patient circulation. Alternatively or additionally, a posterior segment of the brain may be isolated by placing a first (or fifth) catheter to occlude a vertebral artery, a second (or sixth) catheter to occlude another vertebral artery, a third (or seventh) catheter to occlude vertebral vein, and a fourth (or eighth) catheter to occlude another vertebral vein. In either case, by delivering the therapeutic agent through at least one of the catheters positioned within an artery and collecting the perfused agent from at least one of the catheters positioned in a vein, antegrade perfusion of the anterior, posterior, or both segments of the brain may be established. Alternatively, by delivering the therapeutic agent through at least one of the catheters positioned in a vein and collecting the perfused agent from at least one of the catheters positioned in an artery, retrograde perfusion of the brain may be established.

In a fourth exemplary method according to the present invention, the tissue structure is a prostate, the first catheter occludes an inferior vesical artery, and the second catheter occludes an inferior vesical vein. Optionally, a third catheter may be positioned to occlude an internal pudendal artery and/or a fourth catheter may be positioned to occlude an internal pudendal vein. In both cases, the therapeutic agent may be delivered through at least one of the catheters positioned in an artery and collected from at least one of the catheters positioned in a vein to establish antegrade perfusion. Alternatively, the therapeutic agent may be delivered through at least one of the catheters positioned in a vein and collected from at least one of the catheters positioned in an artery to establish retrograde perfusion.

In a fifth exemplary method according to the present invention, the tissue structure is a kidney, the first catheter occludes a renal artery, and the second catheter occludes a renal vein. The therapeutic agent may be delivered through the first catheter and collected from the second catheter to establish antegrade perfusion. Alternatively, the therapeutic agent may be delivered through the second catheter and collected from the first catheter to establish retrograde perfusion.

Additional methods of the invention include isolation and perfusion of:

The bowel, by occluding the superior or inferior mesenteric arteries and the portal vein;

The stomach, by occluding the gastric arteries, and/or other arterial sources, along with the portal vein;

The spleen, by occluding the splenic artery and the portal vein;

The pancreas, by occluding the appropriate branch of the celiac artery and the portal vein;

The testicles or ovaries by occluding the testicular or ovarian arteries and the testicular or ovarian veins;

The pelvic organs such as the uterus, rectum or the bladder, by occlusion of the internal iliac artery or arteries branching therefrom which supply blood to the target organ, and occlusion of the internal iliac vein or veins branching therefrom into which blood from the target organ drains.

Systems according to the present invention comprise at least a first catheter configured for endovascular introduction through a peripheral blood vessel to an inlet artery or other blood vessel supplying blood to the vasculature within the tissue structure. The first catheter may have a first occluding member disposed near its distal end and a first inner lumen extending longitudinally therethrough to a first opening distal to the occluding member. The occluding member is configured to selectively occlude the inlet artery, typically being an inflatable balloon, or mechanical occlusion element such as an umbrella or coated tubular mesh. Alternatively, the system may employ an occluding member which is separate from the catheter, e.g. a loop or snare which may be positioned externally about the blood vessel in which the catheter is placed. By then cinching or otherwise closing the loop or snare against the blood vessel, a lumen of the blood vessel can be isolated so that blood or other media does not flow in an antegrade or retrograde direction past the catheter. Such loops, snares, or other external occlusion devices will typically be placed percutaneously through a small cannula or incision typically while viewing the blood vessel endoscopically on a video monitor. It will also be possible, although generally less preferred, to make a larger surgical incision and place the external occlusion device using more conventional open surgical procedures.

The system further comprises a second catheter configured for endovascular introduction through a peripheral blood vessel to an outlet vein or other blood vessel to which blood flows from the vasculature of the tissue structure. The second catheter may also include an occluding member and a lumen therethrough. Alternatively, the second catheter may be used with a separate, external occlusion device of the type described above in connection with the first catheter. Optionally, the system may include third, fourth, fifth, sixth, seventh, eighth, or possibly more catheters configured for introduction to and occlusion of additional arteries and veins having flow connections to the vasculature of the tissue structure. The system will also include a source of therapeutic agent coupled to a lumen of at least one of the catheters for delivering the therapeutic agent to the tissue structure.

The source of therapeutic agent may comprise only the agent present in a conventional, non-oxygenated carrier, such as saline, glucose, or the like. Preferably, however, the source of therapeutic agent will also comprise an oxygen carrier for delivering oxygen through one or more of the catheters together with the therapeutic agent. Still further preferably, the source of therapeutic agent will comprise a recirculating and oxygenating system for establishing extracorporeal flow between at least two of the catheters and often between more than two of the catheters. The recirculating system may be coupled to the source of therapeutic agent so that the agent may be continuously or intermittently introduced into the recirculating medium. Usually, the recirculating system will comprise at least a pump and an oxygenator, and may optionally comprise further components such as filter, bubble trap, reservoir, or other components of a type which are used in conventional cardiopulmonary bypass circuits. The recirculating system will preferably include an oxygen regulator to allow the oxygen concentration in the circulating medium to be regulated, enabling the delivery of oxygen-rich, oxygen-poor, or normally oxygenated fluids to the organ for optimum therapeutic effect.

As an alternative, the therapeutic agent source may comprise a container for holding a pre-selected volume of an oxygenated medium comprising the therapeutic agent and a separate receptacle for collecting the medium after it has been perfused through the tissue structure. The container of fresh medium may thus be connected to one or more of the catheters to deliver the medium to the vasculature of the tissue structure while the receptacle may be connected to other(s) of the catheters to collect the medium after it has perfused the tissue.

Apparatus according to the present invention still further comprise kits including catheter sets with individual catheters selected for accessing and perfusing particular organs. The kits will include at least one catheter, usually at least two catheters, and frequently including three or more catheters (as described above), where all the catheters comprise a catheter body having a proximal end, a distal end, and a lumen therethrough. An occluding member is preferably disposed near the distal end of the catheter, typically being an inflatable balloon, and each of the catheters is adapted for endovascular introduction through a peripheral blood vessel to position the occluding member within a target blood vessel selected to isolate the desired organ. Alternatively, external occlusion device(s) may be provided which are adapted for externally clamping, cinching, or otherwise closing the blood vessel over the catheter while the catheter is positioned in the lumen of the blood vessel.

Kits may further comprise instructions for use setting forth a method for delivering a medium comprising a therapeutic agent through at least one of the catheters. Generally, the instructions describe one of the methods described herein. Usually, the method set forth in the instructions further comprises collecting the medium through another of the catheters after the medium has perfused the tissue structure. The method set forth in the instructions may still further comprise extracorporeally recirculating and oxygenating the medium from the other catheter before it is returned to the first catheter. The instructions for use may further set forth concentrations, dosages, frequencies of administration, temperatures, pressures, and other information concerning the agent to be delivered. Because the devices and methods of the invention permit complete isolation of a target tissue structure, agents which are unsafe for systemic delivery may be utilized, and known agents may be delivered in a way which might be toxic or otherwise harmful if delivered systemically using conventional techniques. Often, the catheters and instructions are packaged together in a common container, such as a pouch, box, tray, tube, or the like.

A first kit for isolated perfusion of a lung comprises at least two catheters. A first catheter is configured to position the occluding member within a pulmonary artery. A second catheter is configured to position the occluding member within or over at least one of the pulmonary veins. Usually, two catheters are used to occlude the pulmonary veins, the second catheter being configured to position the occluding member in the superior pulmonary vein, and a third catheter being configured to position the occluding member within an inferior pulmonary vein. Alternatively, a single catheter with a diaphragm may be used for occluding both pulmonary veins. The kit may further include a delivery tube positionable in a bronchus for delivering a therapeutic agent into the airways of the lung.

A second kit for isolated perfusion of a liver comprises at least three catheters. A first catheter is configured to position the occluding member within a hepatic artery. A second catheter is configured to position the occluding member within a hepatic vein. A third catheter is configured to position the occluding member within a portal vein.

A third kit for isolated perfusion of a brain comprises at least four catheters. In a first embodiment, a first catheter is configured to position the occluding member within a left internal carotid artery. A second catheter is configured to position the occluding member within a right internal carotid artery. A third is configured to position the occluding member within a left internal jugular vein. The fourth catheter is configured to position the occluding member within a right internal jugular vein. Use of these four catheters will isolate an anterior segment of the brain. In a second embodiment, the first catheter is configured to position the occluding member within a left vertebral artery, the second catheter is configured to position the occluding member within a right vertebral artery, the third catheter is configured to position the occluding member within a left vertebral vein, and the fourth catheter is configured to position the occluding member within a right vertebral vein. Use of the second exemplary kit embodiment will isolate a posterior segment of the brain. A kit may further be provided comprising all eight catheters of both the first and second embodiments for substantially total isolation of the vasculature of the brain.

A fifth kit for isolated perfusion of a prostate comprises at least two catheters. The first catheter is configured to occlude the left or right inferior vesical artery. The second catheter is configured to occlude the left or right inferior vesical vein. Optionally, the kit may comprise a third catheter configured to occlude a left or right internal pudendal artery, and a fourth catheter configured to occlude a left or right internal pudendal vein. The method may be augmented by isolating the ostia of the prostate glands in the urethra using a trans-urethral catheter to allow collection or delivery of agents to the prostate via the prostate glands.

A sixth kit according to the present invention for isolated perfusion of a kidney comprises at least two catheters. The first catheter is configured to position the occluding member within a renal artery, and the second catheter is configured to position the occluding member within a renal vein.

A seventh kit according to the invention for isolated perfusion of a stomach comprises at least two catheters. The first catheter is configured to position an occluding member within a gastric artery, and a second catheter is configured to position the occluding member within the portal vein, or in a hepatic vein.

An eighth kit according to the invention for isolated perfusion of a spleen comprises at least two catheters. The first catheter is configured to position an occluding member within a splenic artery, and a second catheter is configured to position the occluding member within the portal vein, or in a hepatic vein.

A ninth kit according to the invention for isolated perfusion of a small bowel comprises at least two catheters. The first catheter is configured to position an occluding member within a superior mesenteric artery, and a second catheter is configured to position the occluding member within the portal vein, or in a hepatic vein.

A tenth kit according to the invention for isolated perfusion of a large intestine comprises at least two catheters. The first catheter is configured to position an occluding member within a inferior mesenteric artery, and a second catheter is configured to position the occluding member within the portal vein, or in a hepatic vein.

An eleventh kit according to the invention for isolated perfusion of a pelvic organ such as the uterus or the bladder comprises at least two catheters. The first catheter is configured to position an occluding member within an internal iliac artery, and a second catheter is configured to position the occluding member within an internal iliac vein.

A twelfth kit according to the invention for isolated perfusion of a testicle or ovary comprises at least two catheters. The first catheter is configured to position an occluding member within a testicular or ovarian artery, and a second catheter is configured to position the occluding member within a testicular or ovarian vein.

It will be understood that many of the organs and tissue structures susceptible to treatment using the apparatus and methods of the invention have bilateral (left and right) arterial and venous systems, as well as, in some cases, superior and inferior arterial and venous systems, anterior and posterior arterial and venous systems, and other vascular subsystems. It will be understood that the apparatus and methods of the invention may be used to isolate and perfuse any or all of such subsystems simultaneously or independently by subselecting the particular arteries and veins within each vascular subsystem. Thus, for example, the anterior or posterior portion of the brain, left or right lung, left or right kidney, left or right testicle or ovary, and the left or right side of the prostate, uterus, rectum, or stomach, or any subselectable region thereof, may be isolated and perfused individually or together with other regions.

Any of the apparatus and methods described above may be further enhanced by isolated perfusion of lymphatic system. Therefore, the invention further provides an apparatus for isolated perfusion of the lymphatic system comprising at least one catheter configured to position an occluding member in a lymphatic duct selected from the thoracic duct and the right lymphatic duct. Alternatively, the invention provides at least one catheter having at least two occlusion members for isolating an ostium of a lymphatic duct from a vein, usually a subclavian vein.

Some of the apparatus and methods described above, such as those for the liver, kidney, spleen, pancreas, bowel, and stomach, may further benefit from the isolated perfusion of the bile ducts. The invention further provides apparatus and methods for isolated perfusion of the bile ducts. In one embodiment, the apparatus comprises at least one catheter for positioning at least one occluding member into a bile duct. The catheter may be positioned transhepatically, or transesophageally via the duodenum, into, for example, the common bile duct, or the pancreatic duct.

It will be appreciated that the catheters of the present invention will be uniquely configured for accessing particular target sites in a patient's vasculature. For example, the catheter length, shape, diameter, flexibility, dimensions of the balloon or other occluding member, and other characteristics may be appropriately chosen to permit endovascular positioning of the occluding member in the target vessel. Moreover, the catheters may be reinforced with wire or other suitable elements to provide very thin walls and resistance to kinking. In some cases, the catheters may be steerable or preshaped so as to facilitate positioning in the target site. Other aspects of the invention will be apparent from the following detailed description and the accompanying drawings.

BRIEF DESCRIPTION OF THE DRAWINGS

FIGS. 6E–F are side and transverse cross-sections, respectively, of the hepatic vein isolation catheter illustrated in FIG. 6D.

DESCRIPTION OF THE SPECIFIC EMBODIMENTS

Figure 1:
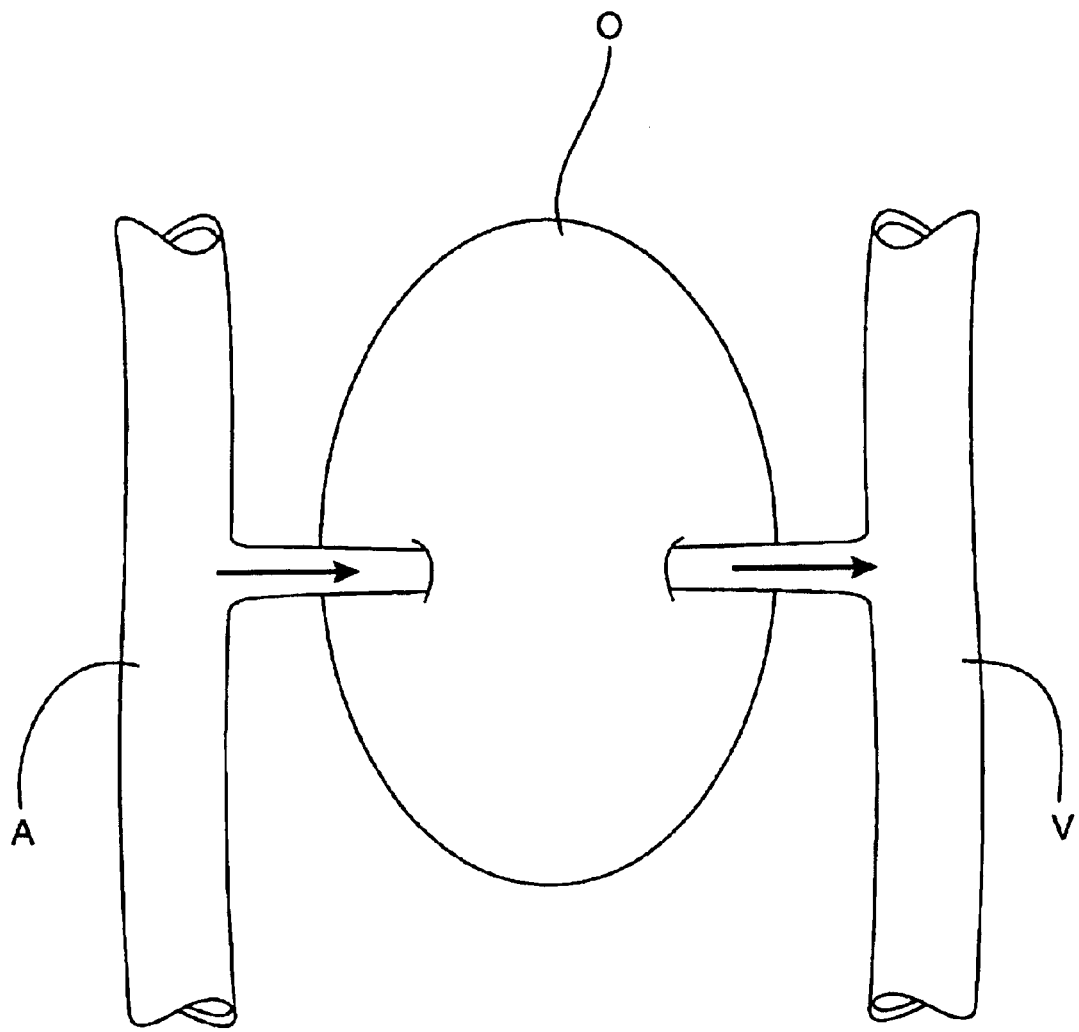
FIG. 1 is a schematic illustration of a tissue structure which may be isolated and perfused according to the methods of the present invention.

Referring now to FIG. 1, a tissue structure in the form of an organ O which may be treated according to the methods of the present invention has an internal vasculature which receives blood from at least one blood vessel carrying oxygenated blood, typically an artery A and which passes blood to another blood vessel, typically a vein V. Thus, blood flow through the organ is generally in the direction of the arrows. It will be appreciated that this is a schematic illustration and that many organs and tissue structures will have more than one artery supplying blood and more than one vein receiving blood. In addition to the blood which is supplied to an organ to oxygenate tissue, some organs receive partially oxygenated blood from another organ or source for processing by the organ, e.g. the liver receives oxygenated blood from the gastrointestinal tract through the portal vein. For simplicity herein, however, those blood vessels which supply blood to an organ or other tissue structure will generally be referred to as arteries and those blood vessel which receive blood from the tissue structures or organs will generally be referred to as veins. In many instances, it may be desirable to occlude and control blood flow from all blood vessels feeding and draining an organ, including those blood vessels responsible for circulating oxygenated blood to the organ tissue as well as those responsible for circulating blood through the organ for processing by the organ. In addition, it may.be desirable in some cases to occlude and control flow within other types of vessels communicating with an organ, such as bile ducts, urinary vessels, the digestive tract, the air passages of the lungs, and the like. Specific instances of such occlusion protocols will be described herein below.

Figure 2:
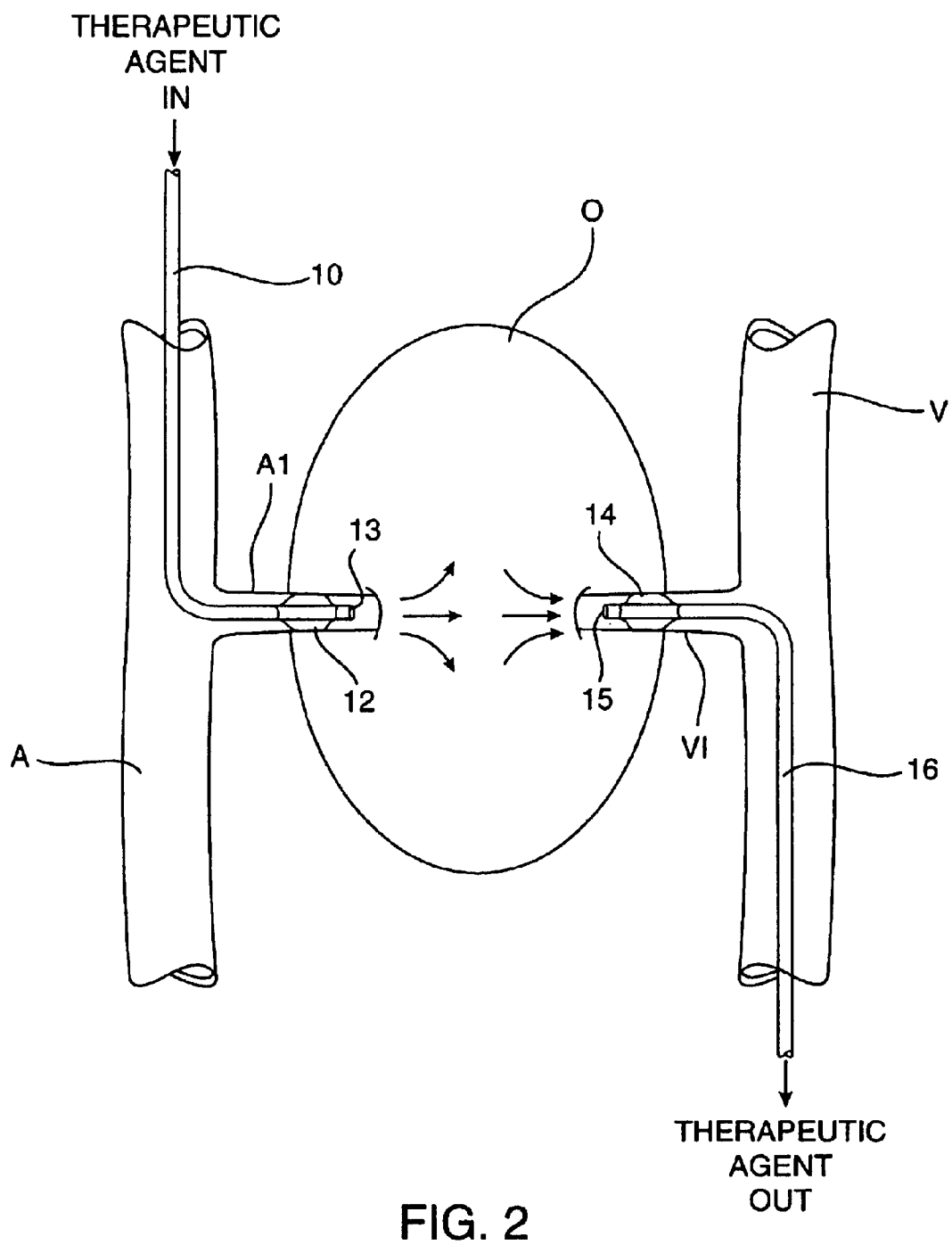
FIG. 2 shows the schematic organ of FIG. 1 being isolated and perfused by a pair of catheters.

Referring now to FIG. 2, exemplary methods for isolating and perfusing an organ O according to the present invention involve positioning a first occluding member, e.g. balloon 12, on catheter 10 within a portion of the artery A1 immediately adjacent to entry of that artery into the vasculature of the organ. Similarly, blood flow from the organ may be occluded by placing balloon 14 or other occluding member on catheter 16 in a segment of the vein V1 which lies immediately adjacent to the outlet of the venous vasculature from the organ O. The catheters 10 and 16 may be endovascularly positioned through peripheral blood vessels and into the target arteries and veins using conventional intravascular access and positioning methods. Once the catheters 10 and 16 are in place, and balloons 12 and 14 inflated to occlude the blood flow, the therapeutic agent may be introduced through a central lumen of catheter 10 out a distal port 13 and into the arterial vasculature of the organ O. The therapeutic agent will perfuse through the arterial vasculature and into the venous vasculature until it reaches the outlet vein segment V1. At that point, it is received in a distal port 15 of catheter 16 and flows outwardly through a lumen of catheter 16 so that it may be collected. In the simplest instance of the present invention, the therapeutic agent may be delivered without an oxygenated carrier, typically in saline, glucose, or other common liquid carrier. More usually, however, the agent will be delivered in an oxygenated carrier capable of delivering oxygen to the organ, usually the patient's own blood or a blood substitute as described below.

Figure 2A:
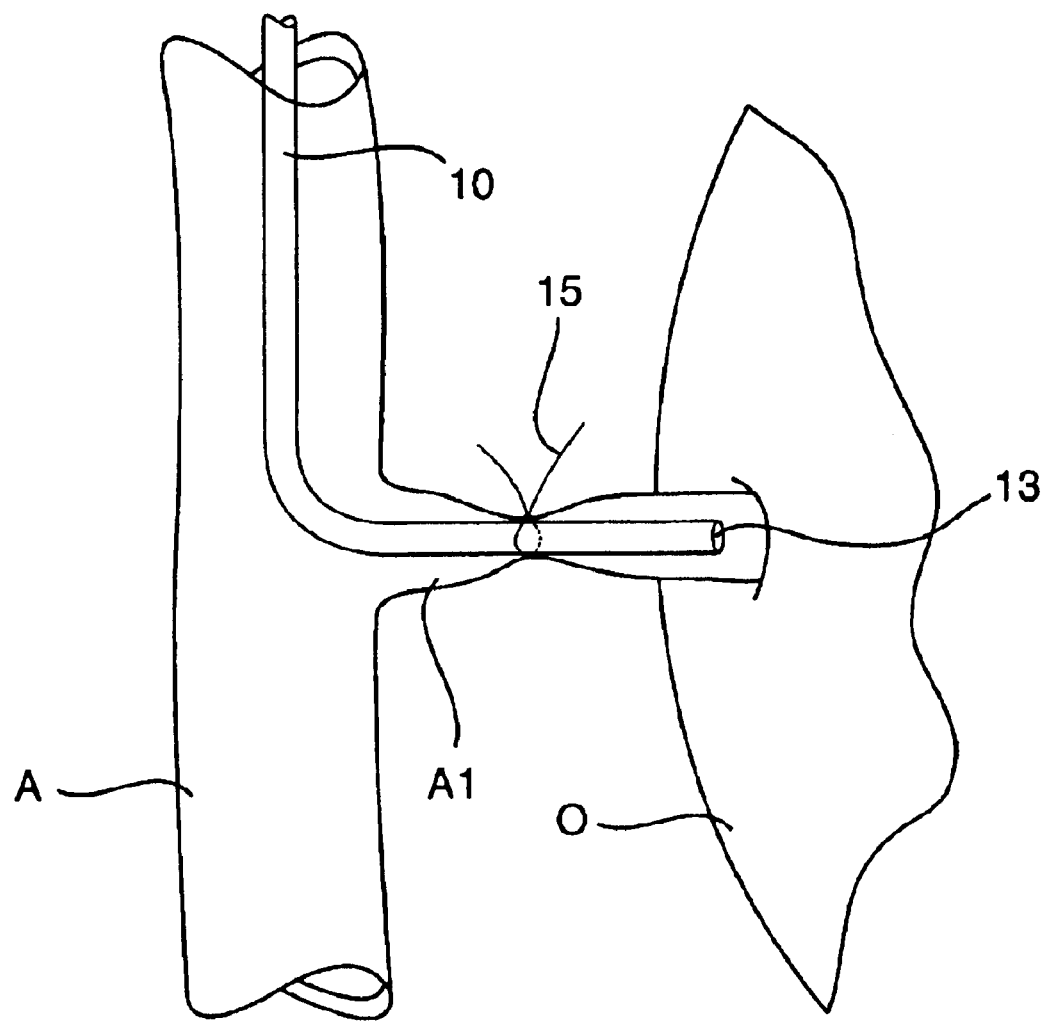
FIG. 2A illustrates an alternative occlusion approach.

While use of a balloon for blood vessel occlusion will generally be preferred, it will also be possible to use other mechanisms and devices for occluding blood flow past the catheter at a location which isolates the target tissue structure from patient's circulation. For example, as illustrated in FIG. 2A, an external loop 15 may be placed on the exterior of the blood so that it seals the internal blood vessel wall against the exterior of the catheter 10. Other external clamps or tourniquets could also be employed. Usually, such external loops or clamps will be placed using a minimally invasive approach where the exterior of the blood vessel is accessed through a percutaneous penetration, typically through a cannula under endoscopic or other viewing systems, e.g. laproscopic, thoracoscopic, or the like. After properly positioning the catheter 10, typically under fluoroscopic observation, the loop 15 or other clamp may then be positioned over the exterior of the blood vessel and tightened down to provide the desired occlusion.

The catheters described herein may be manufactured using any suitable technique and preferably are reinforced in the manner described in published PCT application number PCT/US97/10346, international filing date Jun. 17, 1997, and published PCT application number PCT/US97/03543, international filing date Mar. 7, 1997, each entitled "Cannula and Method of Manufacture and Use," which are hereby incorporated herein by reference. The use of such reinforcement allows the catheters of the invention to have very thin walls for minimum profile and maximum lumen size, while having high kink resistance to enable endovascular positioning through tortuous vessels.

Figure 3:
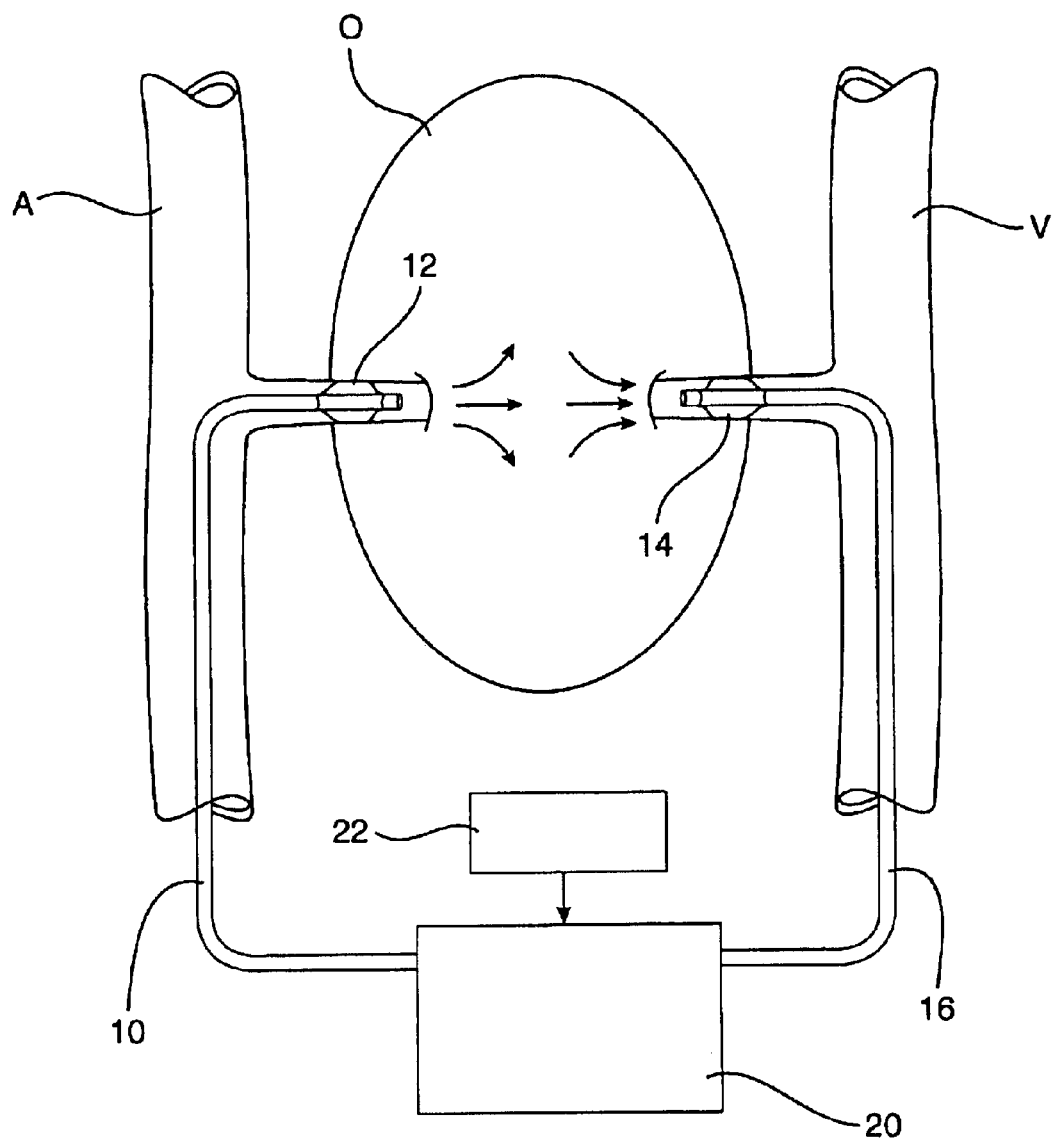
FIG. 3 is similar to FIG. 2, except that perfusion is being effected by an extracorporeal circulation system.

Referring now to FIG. 3, more preferably, the catheters 10 and 16 will be connected to an extracorporeal recirculation system 20 which is capable of recirculating and oxygenating a liquid medium, typically blood but possibly a synthetic oxygen carrier, through the vasculature of organ O. The recirculation system 20 typically comprises at least a pump, an oxygenator, and pressure control means (not illustrated) and will typically also include a filter, bubble trap, reservoir to accommodate excess volume, and other components which are typically utilized in cardiopulmonary bypass systems. A heat exchanger may also be included for controlling the temperature of the recirculating fluid, allowing heating or cooling of the target tissue structure. In some cases, maintaining equal volumes of fluid delivered and returned may be important, so the system will preferably have capability for monitoring and independently controlling the volume of fluid delivered by and returned to the recirculation system. The system may include two separate pumps, one for drainage of blood or fluid, the other for return of blood or fluid, to allow independent control of drainage and return volumes and flow rates. Usually, a separate source of the therapeutic or diagnostic agent 22 will be provided for continuously or intermittently introducing additional therapeutic agent into the recirculating liquid medium. A filter may also be included for selectively removing the agent from the recirculating medium. The system may further include additional reservoirs of saline or other chemical agents, such as histamines, seratonin, calcium, or antihistamines for controlling vascular permeability, oxygen to create hypoxia or hyperoxia, and dyes or other imaging agents. Capacity, flow rate, and other characteristics of the fluid flow through the organ will be selected depending on the particular organ being treated. General considerations for the construction of extracorporeal recirculation and oxygenation systems are described in detail in U.S. Pat. Nos. 5,584,803, 5,478,309; 5,458,574; 5,451,207 and 4,540,399, the full disclosures of which are incorporated herein be reference. The recirculation system will thus have the capability to alter various parameters within the organ, including:

Concentration and volume of the therapeutic or diagnostic agent, by controlling the volume of agent added to the recirculating fluid and/or filtering such agent from the recirculating fluid;

Flow rate of fluid through the organ, by altering the speed of the recirculation pump;

Oxygen concentration, by adding or removing oxygen from the recirculating fluid;

Temperature, by heating or cooling the recirculating fluid;

Hydrostatic pressure, by delivering the recirculating fluid at higher or lower pressures and/or altering the rate of delivery or drainage from the organ;

Osmotic pressure, by altering chemical concentration of the recirculating fluid;

Oncotic pressure, by altering protein concentration;

Vascular permeability, by, for example, adding histamines, anti-histamines or solvents to the recirculating fluid.

By completely isolating the organ from the remainder of the patient's vascular system during administration of a therapeutic medium, the parameters that contribute to the effectiveness of the therapeutic medium on the organ may be maintained at levels which might be harmful if utilized for systemic drug delivery. For example, the temperature of the circulating fluid may be elevated above the systemic temperature (98.6° F.), e.g. over 100° F., preferably 101–105° F., in some cases 106–120° F., to raise organ temperature and enhance efficacy of the therapeutic agent. Similarly, delivery pressures of the fluid medium may be elevated to enhance cellular uptake. Histamines or antihistamines may be delivered to alter vascular permeability within the organ, thereby altering regional fluid volumes. Chemical concentrations within the recirculating fluid may be adjusted to affect osmotic or oncotic pressures within the organ. Therapeutic agents may delivered in larger doses, at higher concentrations, and for longer periods of administration than can be tolerated with systemic delivery. Moreover, with the complete organ isolation provided by the present invention, certain therapeutic agents which are toxic if delivered systemically may be delivered to an isolated organ for heightened therapeutic benefit.

The recirculation system will preferably be configured to first allow circulation through the target tissue structure to be established via the arterial and venous catheters prior to venous and arterial occlusion. The occlusion members are then inflated (or otherwise deployed) to occlude the relevant arteries and veins. Therapeutic agent may then be added into or substituted for the recirculating blood or fluid, and circulated through the tissue structure as desired. The therapeutic agent may then be replaced with a rinsing agent such as saline which is circulated to flush out any remaining therapeutic agent from the tissue structure. The rinsing agent is then replaced with blood, and circulation maintained while the occlusion members are deflated. Circulation through system 20 is then gradually discontinued, and the catheters are removed.

Figure 4:
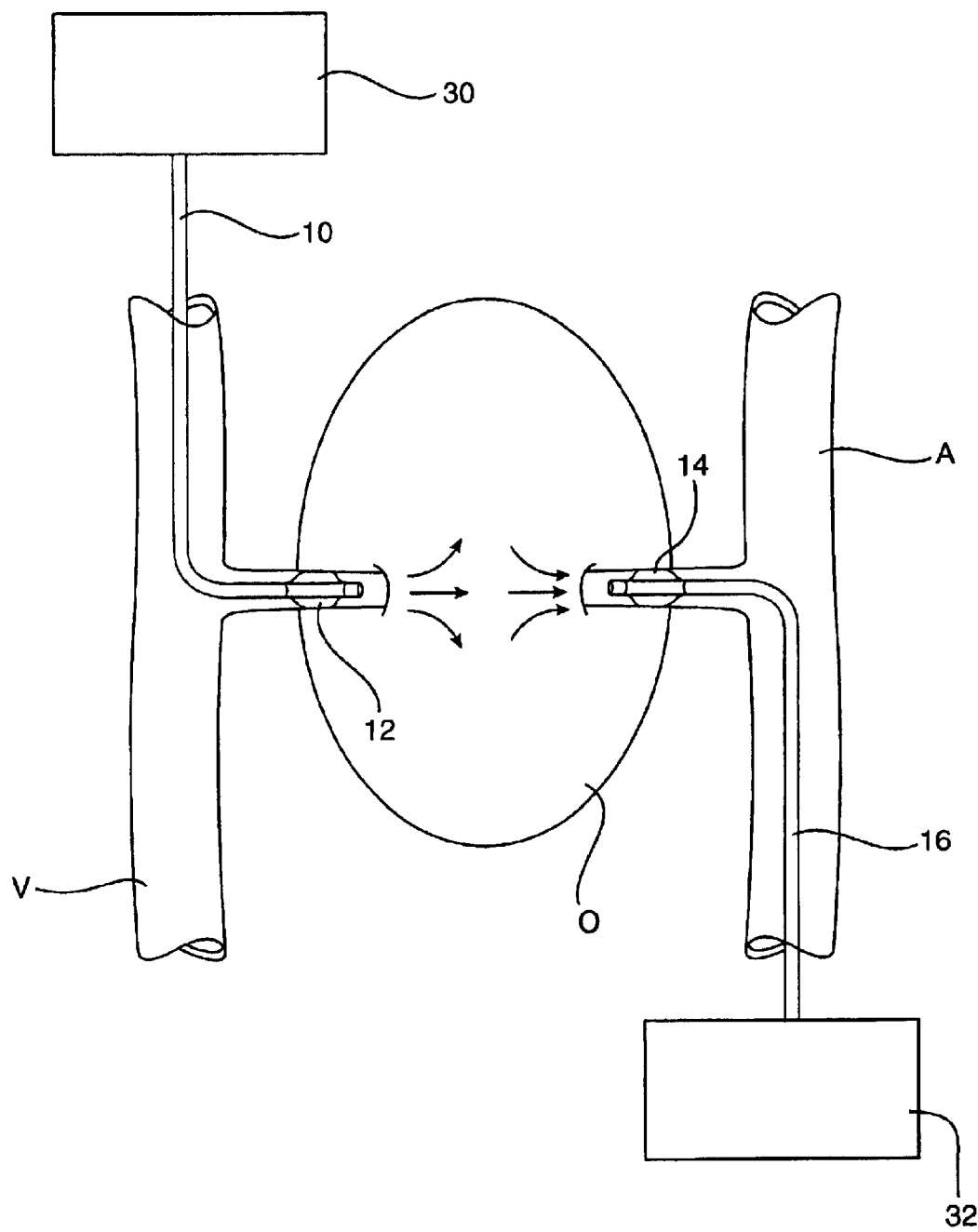
FIG. 4 is similar to FIG. 2 except that perfusion is being effected on a once-through basis.

As an alternative to the recirculating system of FIG. 3, a once-through perfusion system is illustrated in FIG. 4. There, a container 30 which contains a pre-selected volume of oxygenated medium, typically a synthetic medium but possibly blood, is connected to catheter 10. Container 30 will typically be elevated above the patient to deliver the oxygenated medium and therapeutic agent to the patient under a gravity flow although a positive pressure pump may also be used if additional pressure is needed to perfuse the target organ or other tissue structure. The liquid medium will be collected through the second catheter 16 and collected in a receptacle 32. Typically, after collection, the spent medium will be disposed.

In particular instances, it may be desirable to eliminate the step of collecting the perfusate after delivery to the target tissue structure. This may be accomplished by using only the arterial or venous catheter(s) 10 or 16 for delivery of the perfusate using the once-through system of FIG. 4, then allowing the perfusate to dissipate systemically. However, in most cases it will be preferred to collect the perfusate after delivery to minimize any adverse systemic effects of the perfusate.

Figure 5:
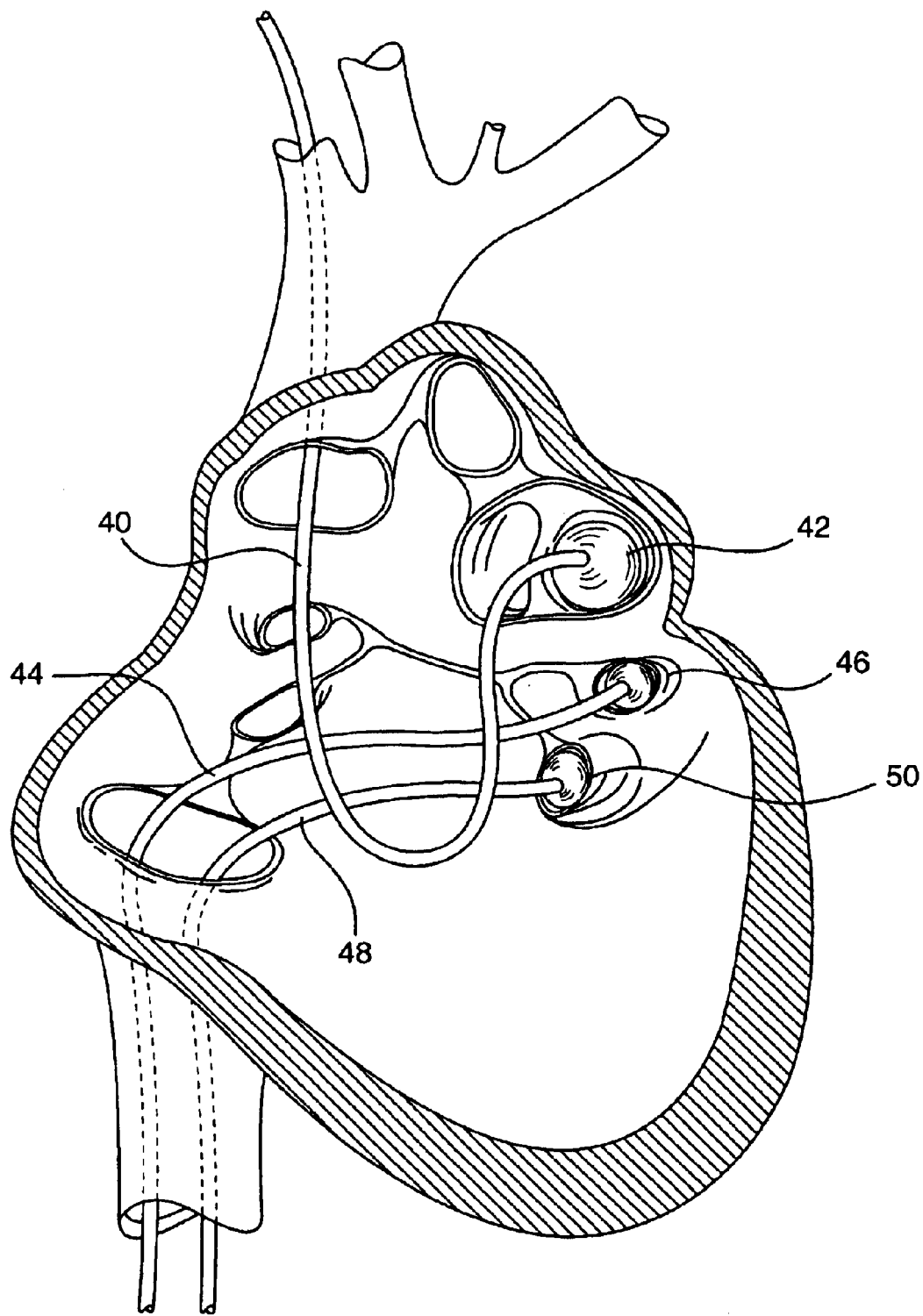
FIG. 5 illustrates use of a three-catheter set for isolating and perfusing a lung according to the methods of the present invention.

Referring now to FIG. 5, an exemplary method and catheter set for isolating and perfusing a lung is illustrated. Isolation of one lung in a patient will preferably be performed while the other lung remains available to receive and return blood from and to the heart although the procedure may also be performed with both lungs being isolated while blood is being oxygenated using an extra corporeal cardiopulmonary bypass system. In the isolated lung, a first balloon catheter 40 is endovascularly introduced, typically through the internal jugular vein and superior vena cava, or from the femoral vein and inferior vena cava, and advanced so that occlusion balloon 42 at its distal end lies within a pulmonary artery which extends from the right ventricle of the heart (the left pulmonary artery being illustrated). A second catheter 44 is percutaneously introduced through the femoral vein and endovascularly advanced across a transseptal puncture into the left atrium so that its distal occlusion balloon 46 lies within a superior pulmonary vein (the left superior pulmonary vein being illustrated). A third catheter 48 is percutaneously introduced through the femoral vein and endovascularly advanced across a puncture in the interatrial septum into the left atrium until occlusion balloon 50 lies within an inferior pulmonary vein. In this approach, it may be desirable to utilize a transseptal sheath introduced from the femoral vein or internal jugular vein into the right atrium, and through the transseptal puncture so as to provide a single lumen through which catheters 46, 48 may be slidably positioned across the interarterial septum. In order to create the septal puncture, a flexible obturator with a blade or other puncturing element at its distal end is positioned in a lumen of the sheath or catheter and advanced through the septum, followed by the sheath or catheter. The obturator is then removed from the patient. As an alternative to the transseptal approach via the venous system, catheters 44, 48 may be introduced into the femoral artery, aorta or other arterial access point and advanced in a retrograde direction through the aorta, across the aortic valve, into the left atrium, and into the pulmonary veins. The catheters utilized in this procedure are typically sized in the range from 14 French (1 French=0.33 mm diameter) to 25 French.

Thus, complete isolation of a single lung is achieved with normal functioning of the contralateral lung. A therapeutic agent may then be infused into the lung either antegrade through catheter 40, or retrograde through catheters 44, 48. The therapeutic agent may be allowed to dwell for a desired time period, then drained by applying negative pressure through any or all of catheters 40, 44, 48. Alternatively, the agent may be continuously circulated through the lung through an extracorporeal pump and treatment system, which receives fluid drained from the lung via catheters 44, 48, preferably filters out any undesirable chemicals or particles, and returns the fluid to the lung via catheter 40. Preferably, the system will include an oxygenator for oxygenating the fluid before return to the lung. In some cases, it may be undesirable to return to the lung any of the fluid drained from it, in which case the treatment agent, which preferably is combined with blood or other oxygen carrier, is delivered from a reservoir through catheter 40 and/or through catheters 44, 48, and the agent (and carrier) are drained from the lung and discarded. Any reduction in blood volume is restored by infusing blood through catheter 40 prior to completing the procedure.

While the apparatus and methods of the invention are useful for the perfusion of organs with various types of therapeutic and diagnostic agents, the inventions is particularly advantageous for the delivery of chemotherapeutic agents for the treatment of cancer, inflammatory disease and other diseases. For example, in the treatment of non-small cell lung cancer, chemotherapeutic agents in current use include cisplatin, paclitaxel, docetaxel, irinotecan hydrochloride, vinorelbine tartrate, and gemcitabine hydrochloride. For small cell lung cancer, chemotherapeutic agents include etoposide, carboplatin, cyclophosphamide, doxorubicin hydrochloride, and vincristine sulfate. Using the apparatus and methods described herein, such agents may be delivered in doses similar in magnitude to those administered systemically, but with significant reduction, if not elimination, of adverse systemic effects. Alternatively, such agents may be delivered in significantly higher doses than the doses which are clinically acceptable for systemic delivery, e.g., 1.5 to 100 times the recommended systemic dose, depending upon the nature of the disease and the agent involved.

Figure 5A:
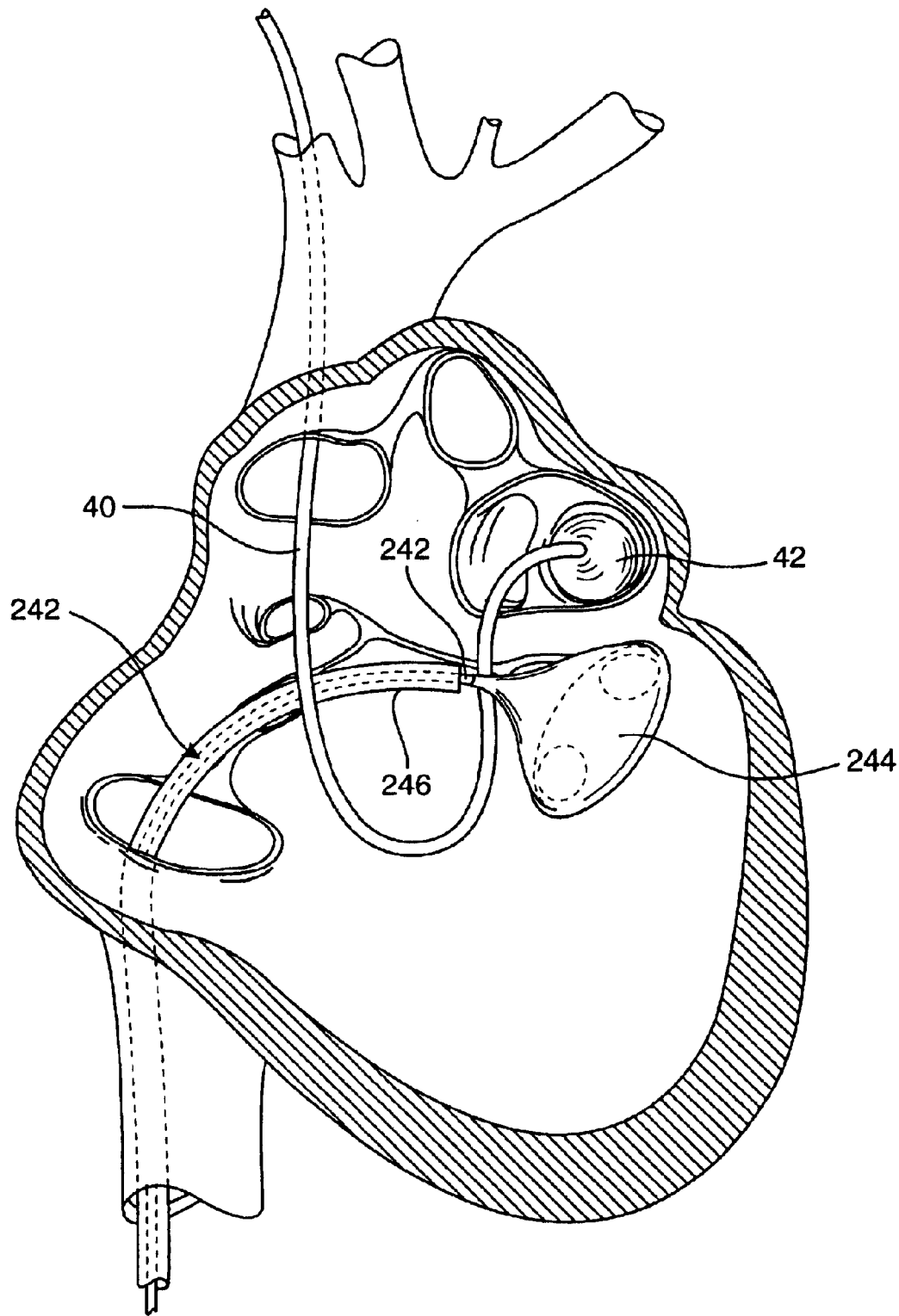
FIG. 5A illustrates the use of a two catheter set and transseptal sheath for perfusing a lung according to the methods of the invention.

Another device and method for isolating the pulmonary veins is shown in FIG. 5A. In this embodiment, a transseptal catheter 242 has a diaphragm 244 at its distal end of sufficient size to surround two pulmonary veins simultaneously. The diaphragm 244 is a flexible and resilient fabric or polymer that may be collapsed to a size small enough for introduction through an endovascular transseptal sheath 246. A lumen (not shown) extends through the catheter to an opening within the diaphragm. The sheath 246 is advanced across the interatrial septum with the diaphragm 244 collapsed within the sheath's inner lumen. The diaphragm 244 is then deployed from the sheath 246 so that it self-expands to its expanded configuration, and the diaphragm is positioned over the ostia of the pulmonary veins. By applying negative pressure through the lumen of the catheter 242, the diaphragm 244 seals against the inner wall of the left atrium, thereby isolating the pulmonary veins.

In an alternative single catheter method of treating the lungs according to the invention, first balloon catheter 40 is advanced into the pulmonary artery and into either the left or right branch thereof, depending upon the lung to be treated. Balloon 42 on the catheter's distal end is inflated to occlude the desired branch of the pulmonary artery. A therapeutic agent is then infused through catheter 40 into the occluded vessel distally of balloon 42, from which the agent flows into the lung tissues. The therapeutic agent is allowed to dwell in the lung for a time period selected to achieve the desired therapeutic effect. Occlusion of the pulmonary artery upstream of the treated lung prevents blood from flushing the agent out of the lung. The therapeutic agent is then drained from the lung by applying negative pressure through the lumen of catheter 40. Balloon 42 is then deflated and catheter 40 is withdrawn from the patient.

A similar procedure may be accomplished in a retrograde manner by positioning catheters 44, 48 in the pulmonary veins and occluding the pulmonary veins using balloons 46, 50, as described above. The therapeutic agent is then infused into the lung in the retrograde direction through the pulmonary venous catheters and allowed to dwell in the lung tissues for the desired time period. Occlusion of the pulmonary veins prevents blood flow through the treated lung from flushing out the agent, although periodic infusions may be desirable. The agent is then drained from the lung by applying negative pressure through catheters 44, 48.

Figure 5B:
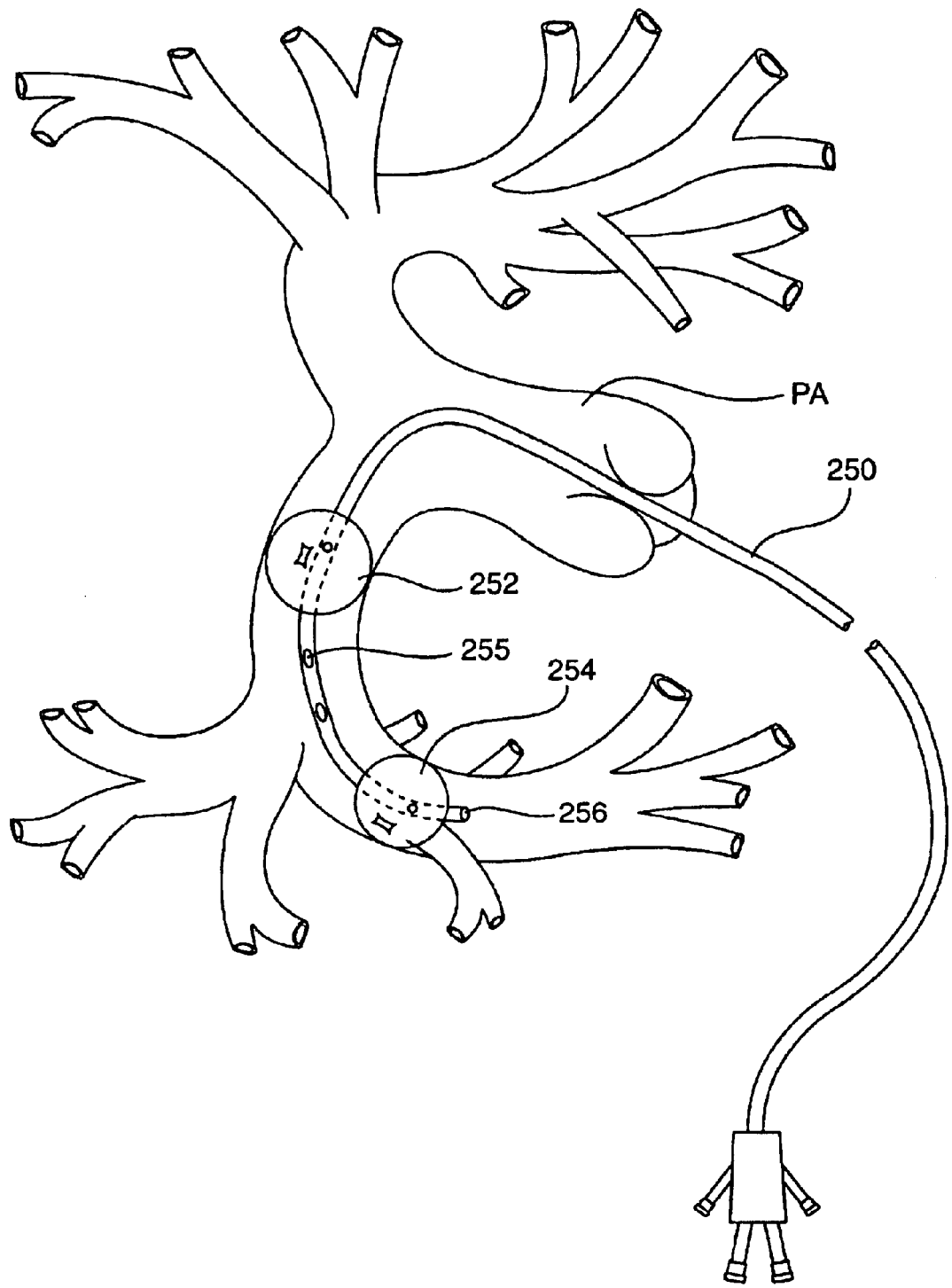
FIG. 5B illustrates the use of a single double-balloon catheter for isolating and perfusing a lung according to the methods of the invention.

FIG. 5B illustrates a further embodiment of a lung isolation and perfusion catheter according to the invention. In this embodiment, catheter 250 has a pair of balloons 252, 254 mounted near its distal end which are sized and configured for occluding selected branches of the left or right pulmonary artery PA. Catheter 250 further includes one or more perfusion outlets 225 between balloons 252, 254 which communicate with a perfusion lumen (not shown) in catheter 250 through which a perfusate may be delivered into the pulmonary artery. A second perfusion outlet 256 at the distal end of catheter 250 communicates with a second perfusion lumen in catheter 250 to allow for delivery of a perfusate and/or blood distally of balloons 252, 254. Optionally, an additional opening (not shown) may be provided proximally of balloons 252, 254 which may communicate with a third perfusion lumen for delivery of perfusate, or which may communicate with the second perfusion lumen to allow for the flow of blood from the proximal side of the balloons to the distal side when the balloons are inflated. In this way, a particular segment, branch or series of branches of the pulmonary artery may be isolated and perfused with affecting other regions distally or proximally of balloons 252, 254. Further, catheter 250 may be used for both delivery and collection of therapeutic agent via the pulmonary artery to eliminate the need for pulmonary venous catheters.

It should be understood that catheter 250 may have various alternative constructions, including having two or more separate shafts slidably coupled to one another, with perfusion lumens and corresponding outlets as well as one or more balloons or other suitable occlusion members disposed on each shaft. The shafts may be coaxially arranged, or coupled together in a parallel arrangement. In this way, the occlusion members and perfusion outlets on each shaft may be independently movable relative to one another for optimum positioning within the pulmonary artery.

For complete isolation of the lung from arterial circulation, it is in some cases further desirable to isolate the bronchial arteries from the aorta. This may be accomplished by placing a double-balloon catheter having a construction similar to that shown in FIGS. 6E–F in the thoracic aorta via the femoral artery. One of the balloons is positioned upstream of the bronchial arteries, while the other is placed downstream of the bronchial arteries. Each balloon is inflated to isolate the bronchial arteries from the aorta. Blood flow across the isolated region is allowed through the perfusion lumen in the catheter, which will be of sufficient size to provide adequate blood flow through the aorta to sustain the patient during treatment. Therapeutic and other agents may be delivered into or collected from the bronchial arteries through the openings disposed between the two balloons.

Any of the aforementioned lung treatment procedures may be enhanced by concurrent delivery of a therapeutic agent, sensitizing agent, potentiating agent, bronchial blocker, steam, solvent, or other suitable substance into the airways of the lung via the bronchus. For example, vasomotor tone may be modified by altering the gas mixture in the lung, thereby altering local pulmonary circulation and enhancing selectivity of the therapeutic agent to the target lung tissues. Selective ventilation of the lung may also be used to induce hypoxia in selected regions, thereby stimulating pulmonary vasoconstriction in such regions so as to reduce uptake of the therapeutic agent delivered via the pulmonary artery. Vasodilating agents or vasoconstricting agents may be delivered into selected regions of the lungs to alter pulmonary vasoconstriction. Hot or cold fluids may also be introduced to alter vasoconstriction or other parameters. In this procedure, a delivery tube is placed via the trachea into the left or right bronchus in communication with the lung to be treated. Branches of the bronchus may be subselected for delivery to a specific region of the lung.

Preferably, the delivery tube will include a balloon for occluding the bronchus to facilitate containment of the agent within the treated lung. The agent may be in liquid, gas, aerosolized powder or other suitable form for introduction into the lung via the delivery tube. Certain agents may be transferred via the alveoli into the blood vessels communicating with the pulmonary artery, where such agents may be drained from the patient using any of the catheters described above. Other agents affecting vasoconstriction, vasomotor tone, vascular permeability or other parameters may remain in the lung. Any agent remaining within the airways of the lung may be collected by applying negative pressure through the delivery tube.

Figure 6A:
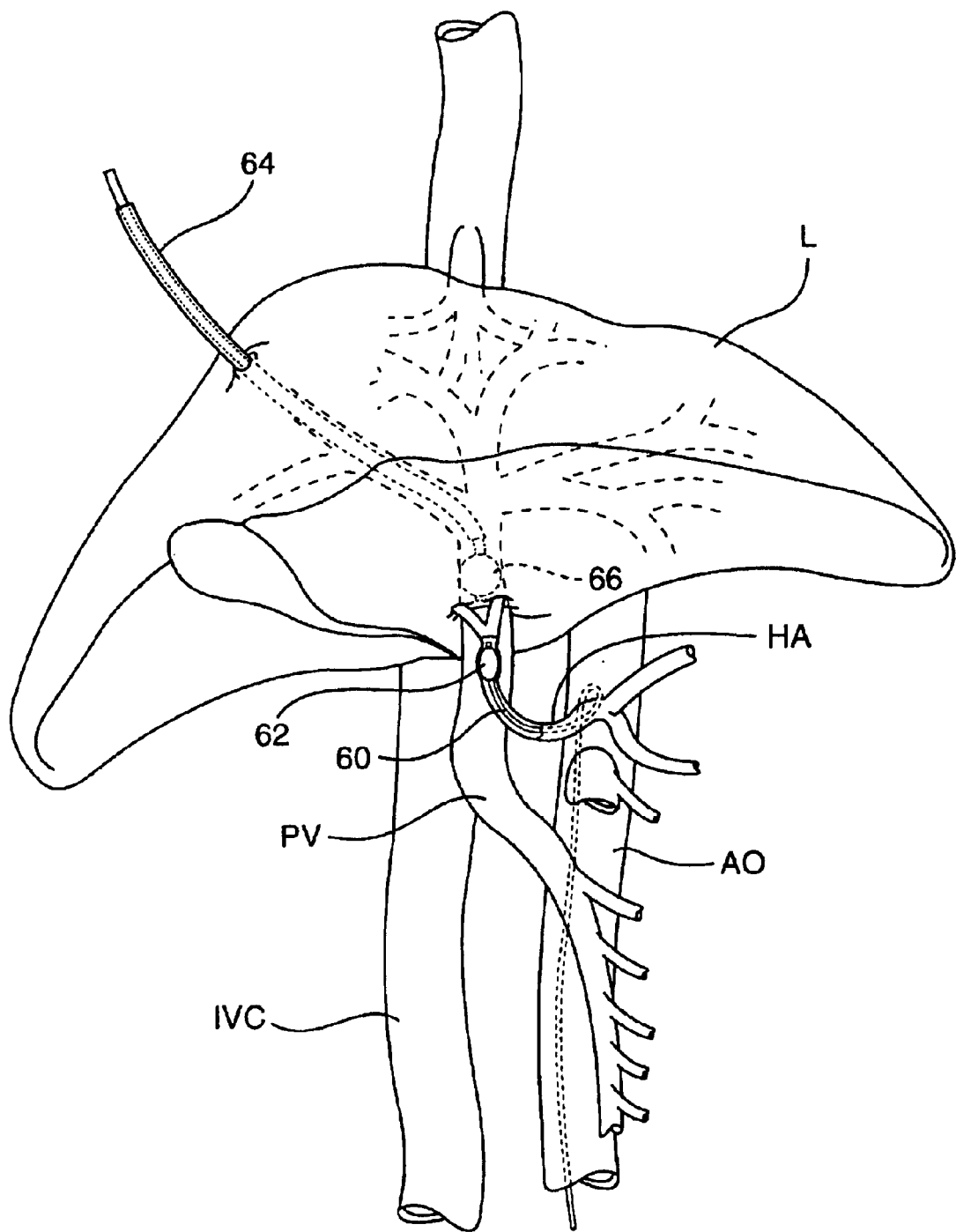
FIGS. 6A and 6B illustrate use of a three-catheter set for isolating and perfusing a liver according to the methods of the present invention.
Figure 6B:
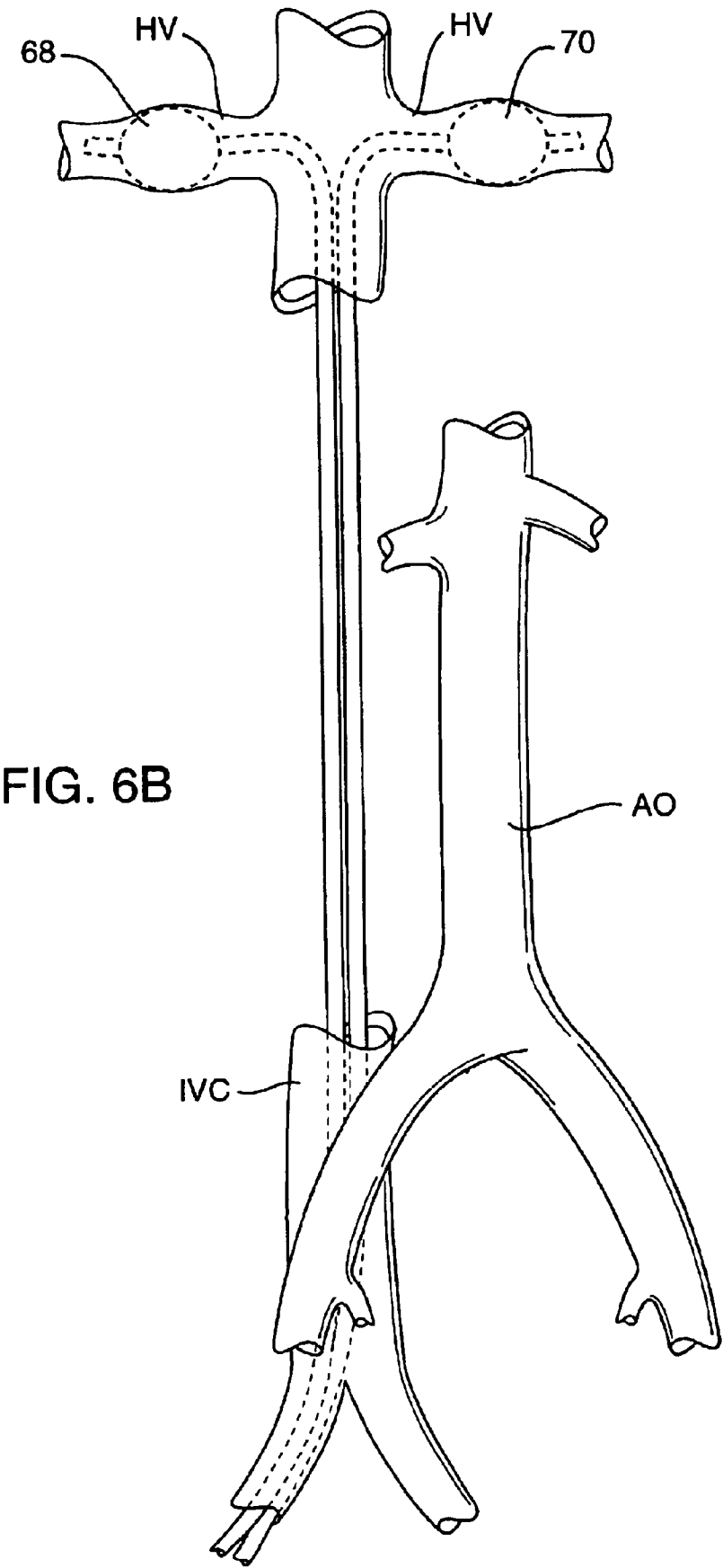

Referring now to FIGS. 6A and 6B, isolation and perfusion of the liver will be described. As mentioned above, the liver L receives blood flow from the portal vein PA as well as from the hepatic artery HA. Catheter 60 may be introduced through the aorta AO via the femoral artery and into the hepatic artery, where balloon 62 may be inflated to include the hepatic artery. Occlusion of the portal vein PV may be achieved by introducing a catheter 64 transhepatically, via a transhepatic puncture, into the portal vein or a branch thereof so that balloon 66 may be inflated and occlude the portal vein. The transhepatic puncture is preferably created by means of a removable guidewire or obturator positionable in the lumen of catheter 64 and having a distal tip suitable for penetrating through the liver tissue. Alternatively, a separate sheath may be utilized to create the transhepatic puncture, and catheter 64 may then be positioned through the sheath. In this embodiment, catheter 64 is introduced transabdominally through an abdominal incision, trocar, or other suitable access device. The portal vein PV and its branches may be identified using transabdominal ultrasound, fluoroscopy or magnetic resonance imaging. Catheter 64 may be removed after each use, or implanted into the portal vein for a period of days, weeks or even months with its proximal end extending out of the patient's abdomen to permit periodic infusions of therapeutic agent.

Figure 6C:
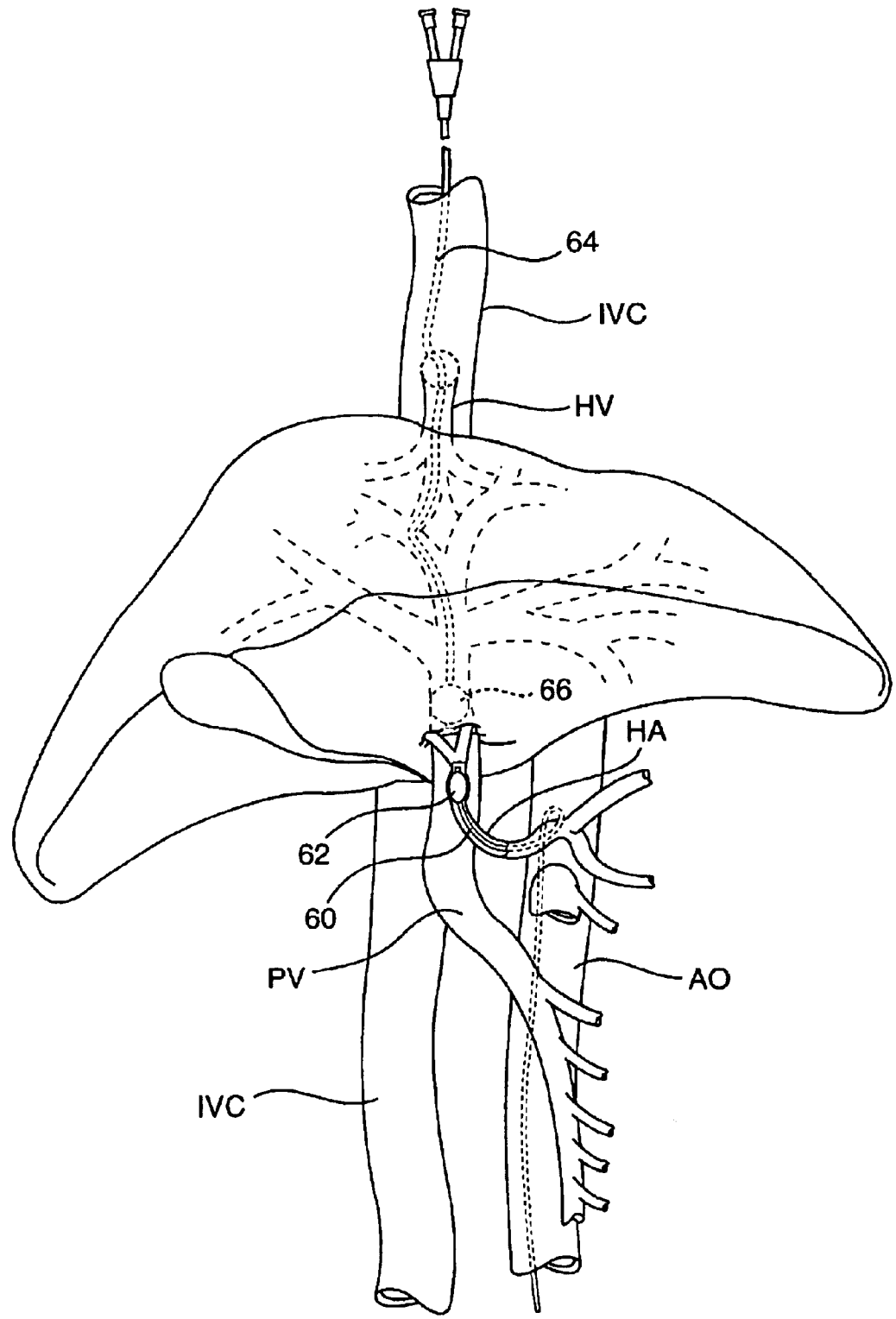
FIG. 6C illustrates an alternative device and method for occluding the portal vein according to the principles of the invention.

In an alternative method of portal vein catheterization, shown in FIG. 6C, catheter 64 is introduced from a peripheral vein such as the jugular vein (as shown) or femoral vein (not shown), and through inferior vena cava (IVC) to the hepatic veins HV, where it is advanced into the liver. Catheter 60 is then advanced through a transhepatic puncture into a branch of the portal vein within the liver. Such a vein may be identified using transabdominal ultrasound or magnetic resonance imaging. Catheter 60 may then be advanced endovascularly into the portal vein PV and balloon 66 inflated to occlude the portal vein.

Figure 6D:
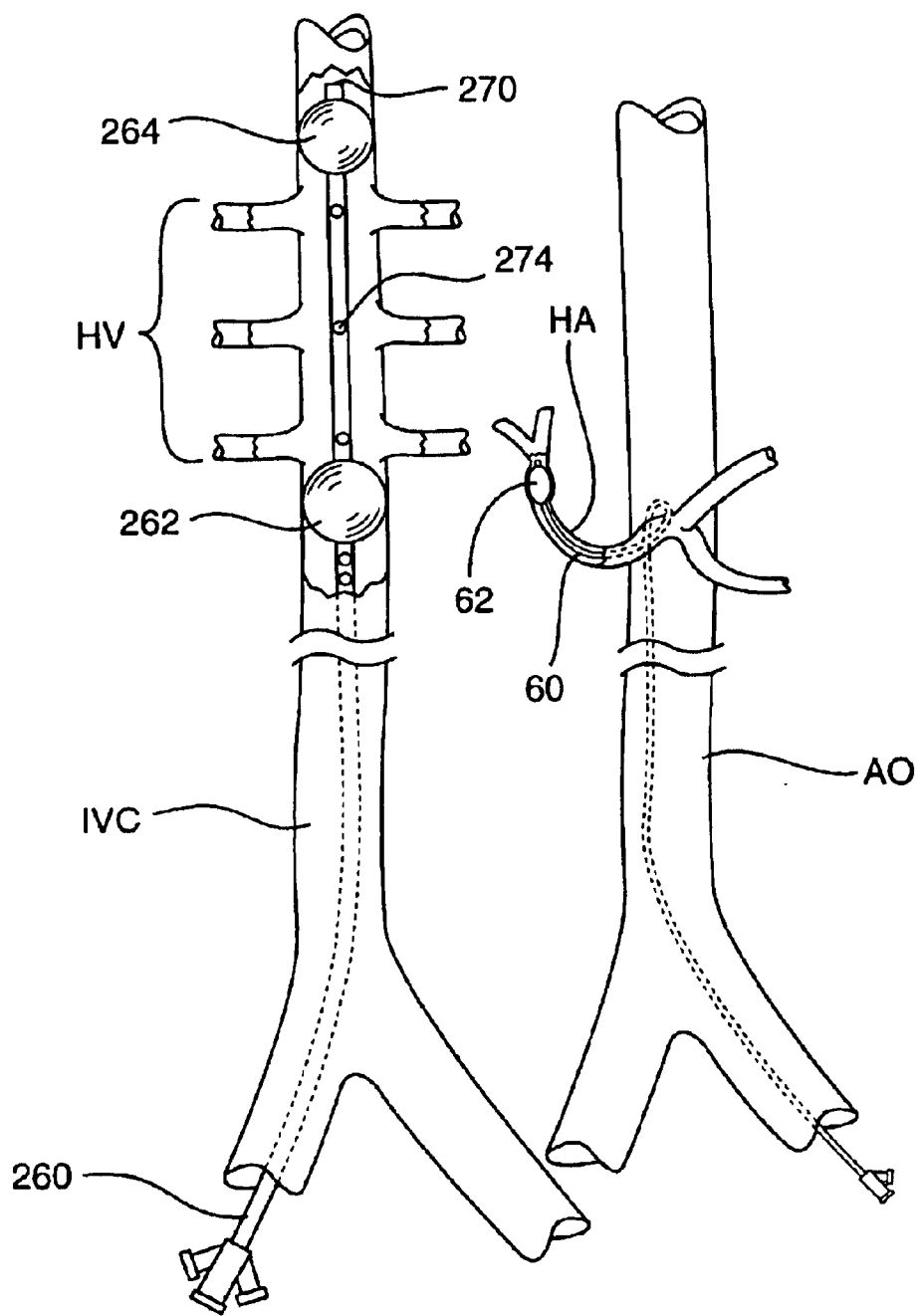
FIG. 6D illustrates an alternative device and method for isolating the hepatic veins from the inferior vena cava according to the principles of the invention.

On the venous side, blood flow from the liver may be occluded by positioning occluding balloons 68 and 70 within the hepatic veins HV via the IVC from a peripheral vein such as the femoral vein, as illustrated in FIG. 6B. Alternatively, as shown in FIGS. 6D–F, a catheter 260 may be introduced through the IVC and proximal and distal balloons 262, 264 on the catheter may be inflated to occlude the IVC both upstream and downstream of the hepatic veins HV. Blood flow across the isolated region of the IVC is permitted through a perfusion lumen 266 extending through the catheter from inlet holes 268 on the proximal side of the proximal balloon 262 to an outlet hole 270 distal to the distal balloon 264. A drainage lumen 272 communicates with one or more drainage inlets 274 between balloons 262,264 to allow for drainage of blood and perfusate from the hepatic veins HV. Inflation lumens 273, 275 are in comunicationn with balloons 262,264, respectively, for delivering inflation fluid thereto. As an alternative to the embodiment shown, two separate catheters may be utilized, one positioned from the femoral vein to position a balloon in the IVC inferior to the hepatic veins HV, and a second positioned from the internal jugular vein through the heart into the IVC to position a balloon superior to the hepatic veins HV. The catheters utilized in this procedure are typically sized in the range from 14 French (1 French=0.33 mm) to 25 French.

It will be understood that the foregoing method for perfusing the isolated liver may be simplified by eliminating catheterization of the portal vein and relying upon delivery (or collection) of therapeutic agent solely from the hepatic artery, and collection (or delivery) solely from the hepatic vein. This method will have particular success where the region of the liver to be treated receives its arterial blood supply from the hepatic artery, rather than the portal vein. In the event that any of the agent delivered reaches the portal vein, portal venous pressures will usually be high enough to prevent retrograde flow of such agent through the portal vein to other structures. This simplified method may also be facilitated by operating the recirculation system in such a way as to ensure that the volume of therapeutic agent/recirculating medium delivered is equal to that collected.

Figure 6G:
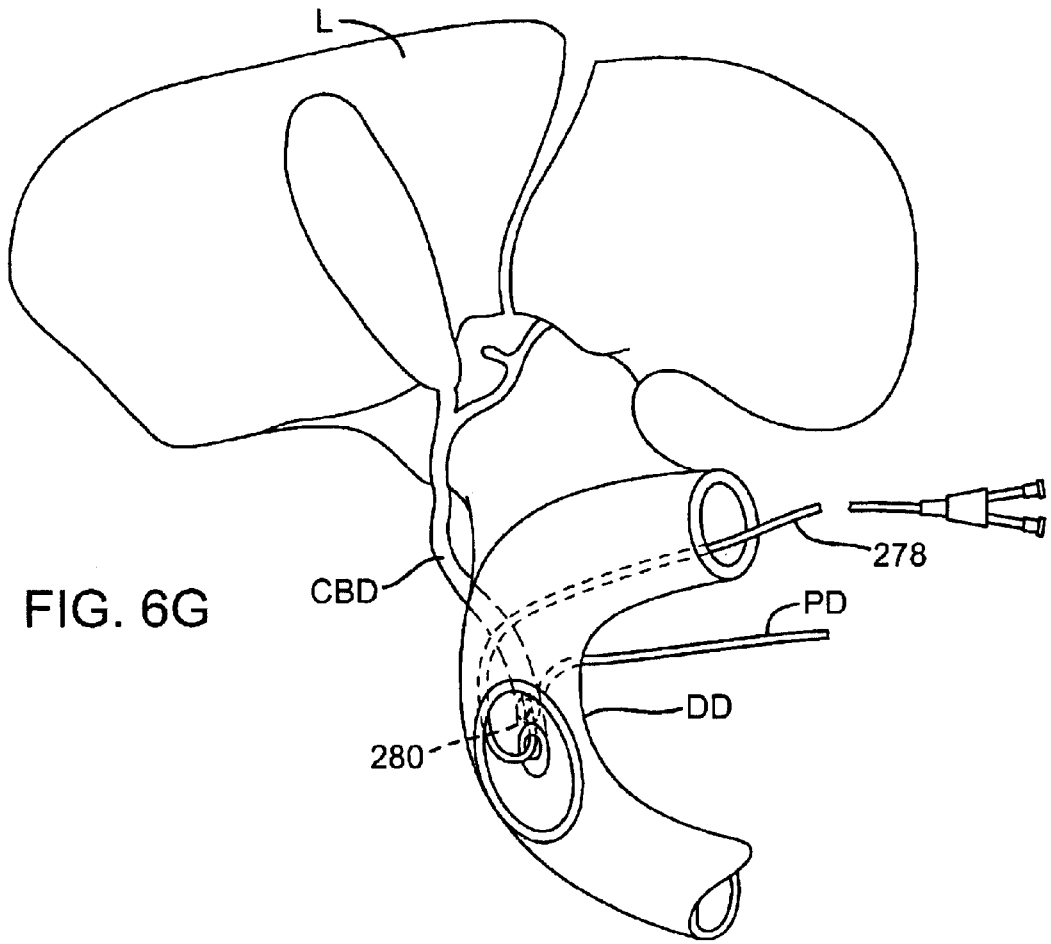
FIGS. 6G–H illustrate the use of a catheter for occluding a common bile duct and a pancreatic duct, respectively, according to the principles of the invention.

The procedure for isolating and perfusing the liver just described may be enhanced by catheterization and occlusion of the bile ducts leading out of the liver. As illustrated in FIG. 6G, a catheter 278 may be introduced through the esophagus and stomach into the duodenum DD, from which the catheter may be positioned in the common bile duct CBD, allowing balloon 280 to be inflated to occlude the duct. Perfusate may thus be drained from or perfused into the bile ducts through catheter 278.

Figure 6H:
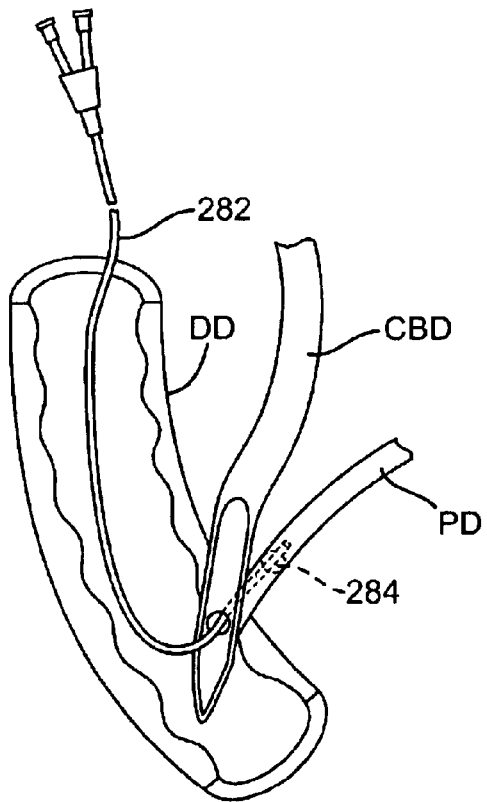

Isolation and perfusion of the pancreas is also enabled by placement of a first occlusion catheter (not shown) via the aorta in the gastroduodenal artery or superior pancreaticoduodenal artery, which branch from the celiac trunk, and by placement of a second occlusion catheter in the portal vein as described above. Alternatively, a catheter may be positioned in or around the hepatic veins via the IVC as described above in connection with FIGS. 6B and 6D, although occlusion and collection of the agent in the portal vein is usually preferred to avoid exposure of the liver to the agent. As shown in FIG. 6H, a catheter 282 may also be positioned via the duodenum DD into the pancreatic duct PD, which may be occluded by means of balloon 284, for perfusion or drainage of the pancreas via the bile duct.

Figure 7:
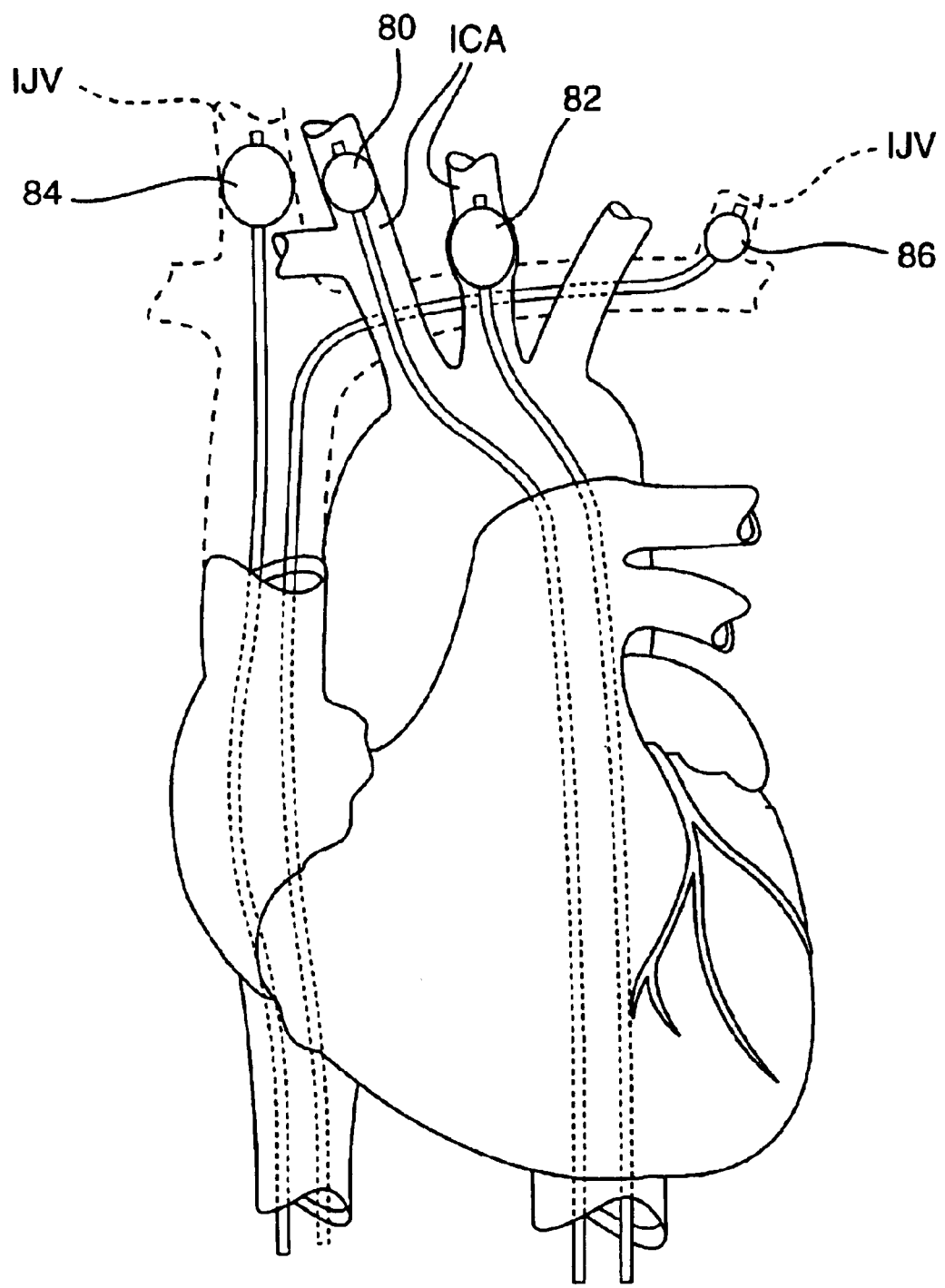
FIG. 7 illustrates use of a four-catheter set for isolating and perfusing an anterior segment of the brain according to the invention.

Referring now to FIG. 7, isolation and perfusion of the brain preferably utilizes a four-catheter set. In particular, an anterior segment of the brain may be isolated by occluding the right and left internal carotid arteries ICA using balloons 80 and 82 which may be introduced in a conventional manner, e.g. via the femoral artery. Blood flow from the anterior segment of the brain is blocked with balloons 84 and 86 placed in the right and left interior jugular veins IJV, respectively. Balloons 84 and 86 may be introduced in a conventional manner, via the femoral or internal jugular veins. Once in place, the anterior segment of the brain may be perfused in an antegrade manner by introducing the therapeutic agent (optionally in combination with an oxygen carrier as described above) through either or both of the arterial cannulas and collecting the perfusate after it is passed through the brain vasculature via either or both of the venous catheters. In order to enhance both the rate and completeness of perfusion, it will usually be desirable to use all four catheters for introducing and collecting the perfusate. Retrograde perfusion may be accomplished in an analogous manner where either or both of the venous catheters are used for introducing the therapeutic agent and either or both of the arterial catheters are used for collecting the perfusate after it has passed through the vasculature.

Figure 7A:
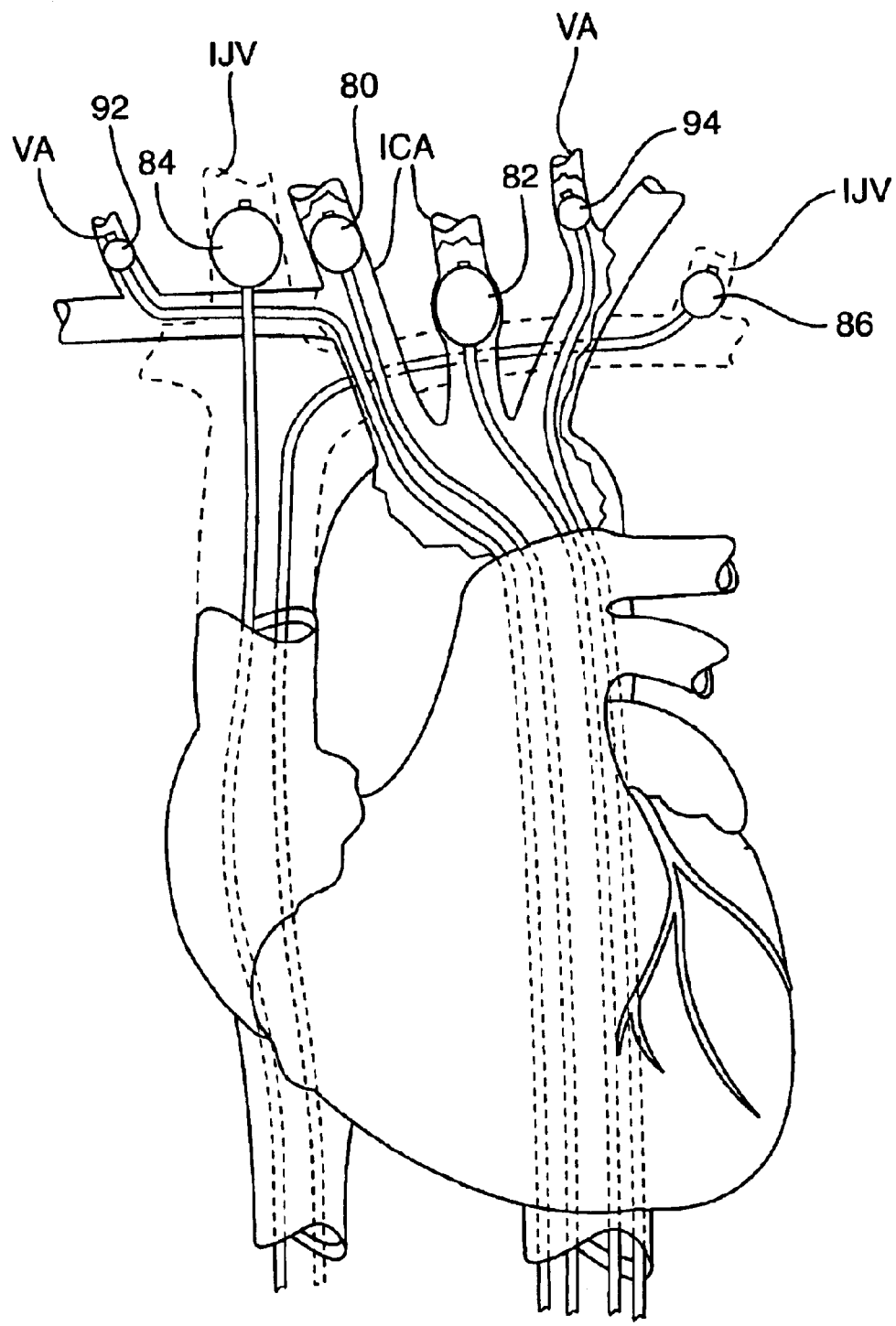
FIG. 7A illustrates the use of a six-catheter set for isolating and perfusing an anterior or posterior segment of the brain according to the invention.

Both anterior and posterior segments of the brain may be isolated and perfused using a six catheter set as shown in FIG. 7A. Arterial catheters are used to position balloons 92 and 94 in the right and left vertebral arteries VA, respectively, as well as in the left and right internal carotid arteries ICA as described above. Venous isolation is achieved by the use of occlusion balloons 84, 86 in the left and right internal jugular veins IJV, as described above, or for posterior isolation only, by placing balloon occlusion catheters into the vertebral veins (not shown). Perfusion of the anterior or posterior segments of the brain may be achieved using these catheters to introduce the therapeutic agent and perfusate in an antegrade or retrograde manner analogous to that described for the anterior segment of the brain. The catheters utilized in this procedure are typically sized in the range from 14 French (1 French=0.33 mm) to 25 French.

Figure 8:
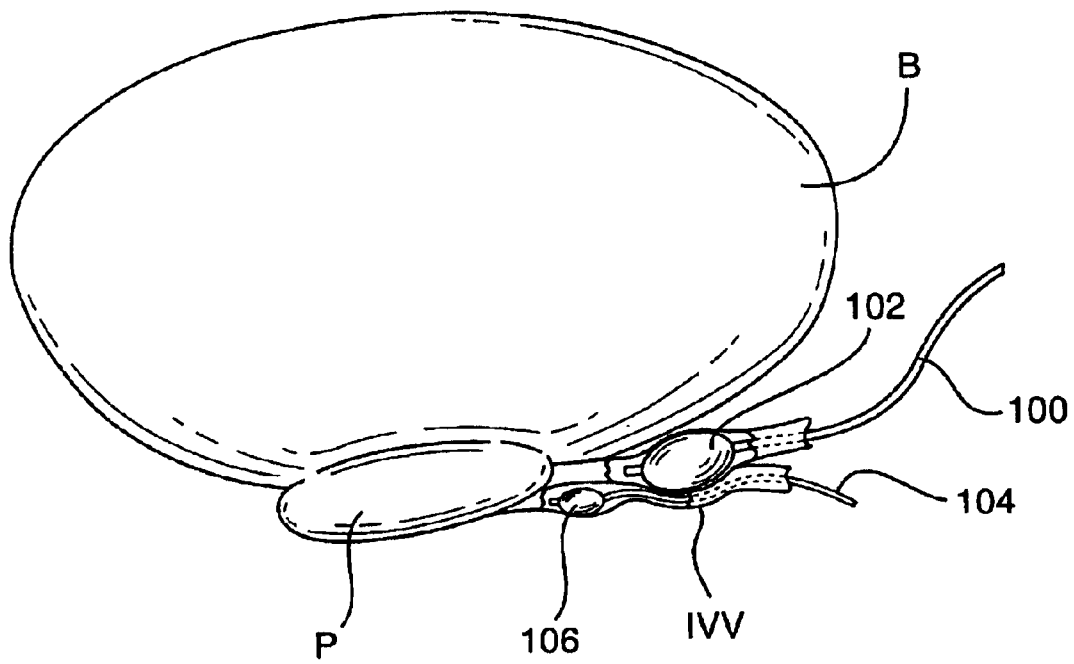
FIG. 8 illustrates use of a two-catheter set for isolating and perfusing the prostate according to the invention.

Referring now to FIG. 8, a prostate P may be isolated and perfused according to the present invention using a two-catheter set. Prostate P is positioned beneath the bladder B, and a first catheter 100 is used to position an occluding balloon 102 in the inferior vesical artery IFA via the internal iliac artery (not shown). Alternatively, if the inferior vesical artery cannot be subselected, the internal iliac artery may be occluded upstream of the branching point of the inferior vesicle artery. Blood returning to the venous side of the circulatory system may be blocked using a balloon 106 positioned using catheter 104 in the inferior vesical vein IVV or in the internal iliac vein. In this way, the majority of the blood supply to and from the vasculature of the prostate P is blocked. If further isolation is desired, balloon catheter may be placed in the internal pudendal artery and internal pudendal vein which provide for a small portion of the blood circulation within the prostate vasculature. The therapeutic agent may then be introduced via either or both of the arterial catheters and collected via either or both of the venous catheters in order to establish antegrade perfusion. Conversely, retrograde perfusion may be established by introducing the therapeutic agent via either or both of the venous catheters and collecting the perfusate via either or both of the arterial cannulas. This may be performed on either right side (via the right internal iliac artery and vein), the left side (via the left internal iliac artery and vein), or both. The catheters utilized in this procedure are typically sized in the range from 14 French (1 French=0.33 mm) to 25 French.

Isolation and perfusion of the prostate may be augmented by placing a catheter in the urethra to isolate the prostate glands to allow delivery or collection of agent from such glands. A double balloon catheter having a construction similar to catheter 260 of FIGS. 6E–F may be positioned in the urethra with a balloon positioned on either side of the openings of the prostate glands. In this way, the prostate glands are isolated from the urethra, yet a perfusion lumen in the catheter allows fluid flow past the occluded region. Therapeutic or other agents may then be delivered into or collected from the prostate glands through the openings between the balloons.

Figure 9:
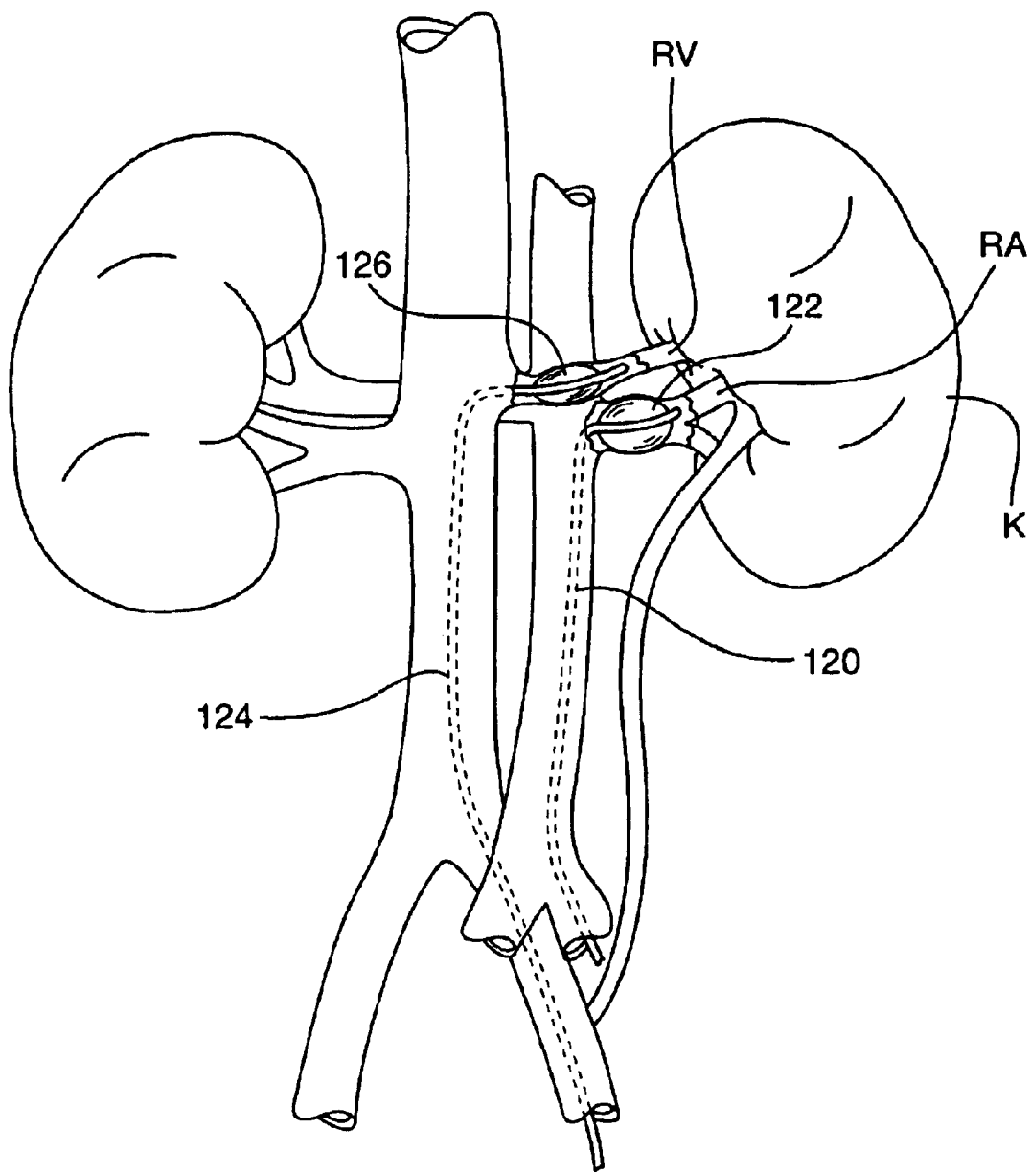
FIG. 9 illustrates use of a two-catheter set for isolating and perfusing a kidney according to the invention.

Referring now to FIG. 9, isolation and perfusion of a kidney K will be described. Usually, a two-catheter set is sufficient for achieving substantially complete isolation. An arterial cannula 120 is used to position an occluding balloon 122 in the renal artery RA, usually before the renal artery branches into two segments. The arterial cannula 120 may be introduced the via the femoral artery through the abdominal aorta in a conventional manner. A venous catheter 124 may be used to position occluding balloon 126 within the renal vein RV. The venous catheter 124 may be introduced via the femoral vein and inferior vena cava in a conventional manner. Once the catheter 120 and 124 are positioned and the occluding balloons 122 and 126 deployed, the kidney K may be perfused with a therapeutic agent in an antegrade direction from the arterial catheter to the venous catheter or in a retrograde direction from the venous catheter to the arterial catheter. The catheters utilized in this procedure are typically sized in the range from 14 French (1 French =0.33 mm) to 25 French.

In conjunction with isolation and perfusion of the kidney, it may be desirable to occlude the ureter and to deliver therapeutic agents or drain fluids therefrom. This may be accomplished by placing a balloon catheter through the urethra into the bladder, where the opening of one or both of the ureters may be catheterized and occluded.

Figure 10:
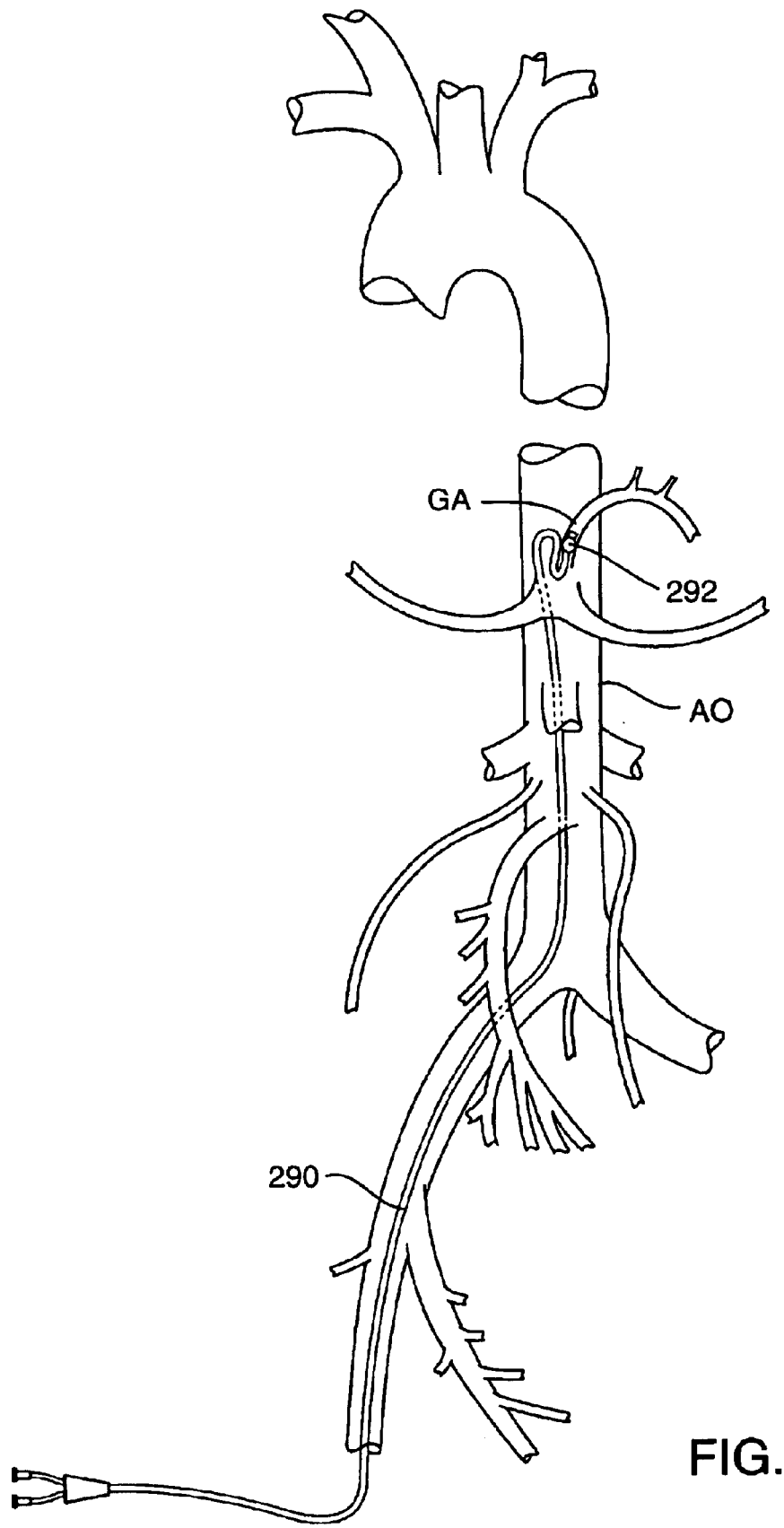
FIG. 10 illustrates the use of a catheter for isolating and perfusing the stomach according to the invention.

Referring to FIG. 10, a method of isolating and perfusing the stomach according to the invention includes positioning a catheter 290 from the femoral artery through the abdominal aorta and the celiac trunk into the gastric artery GA. An occlusion balloon 292 is then expanded to occlude the gastric artery GA. Either the right, left, superior or inferior regions of the stomach may be subselected by placing occlusion catheters in the corresponding arteries for those regions, which include the right and left gastric arteries, the right and left gastroepiploic arteries, and the gastroduodenal artery. On the venous side, a catheter is positioned into the portal vein PV as described above in connection with FIGS. 6A–C. Alternatively, a catheter may be positioned in or around the hepatic veins via the IVC as described above in connection with FIGS. 6B and 6D, although occlusion and collection of the agent in the portal vein is usually preferred to avoid exposure of the liver to the agent.

Figure 11:
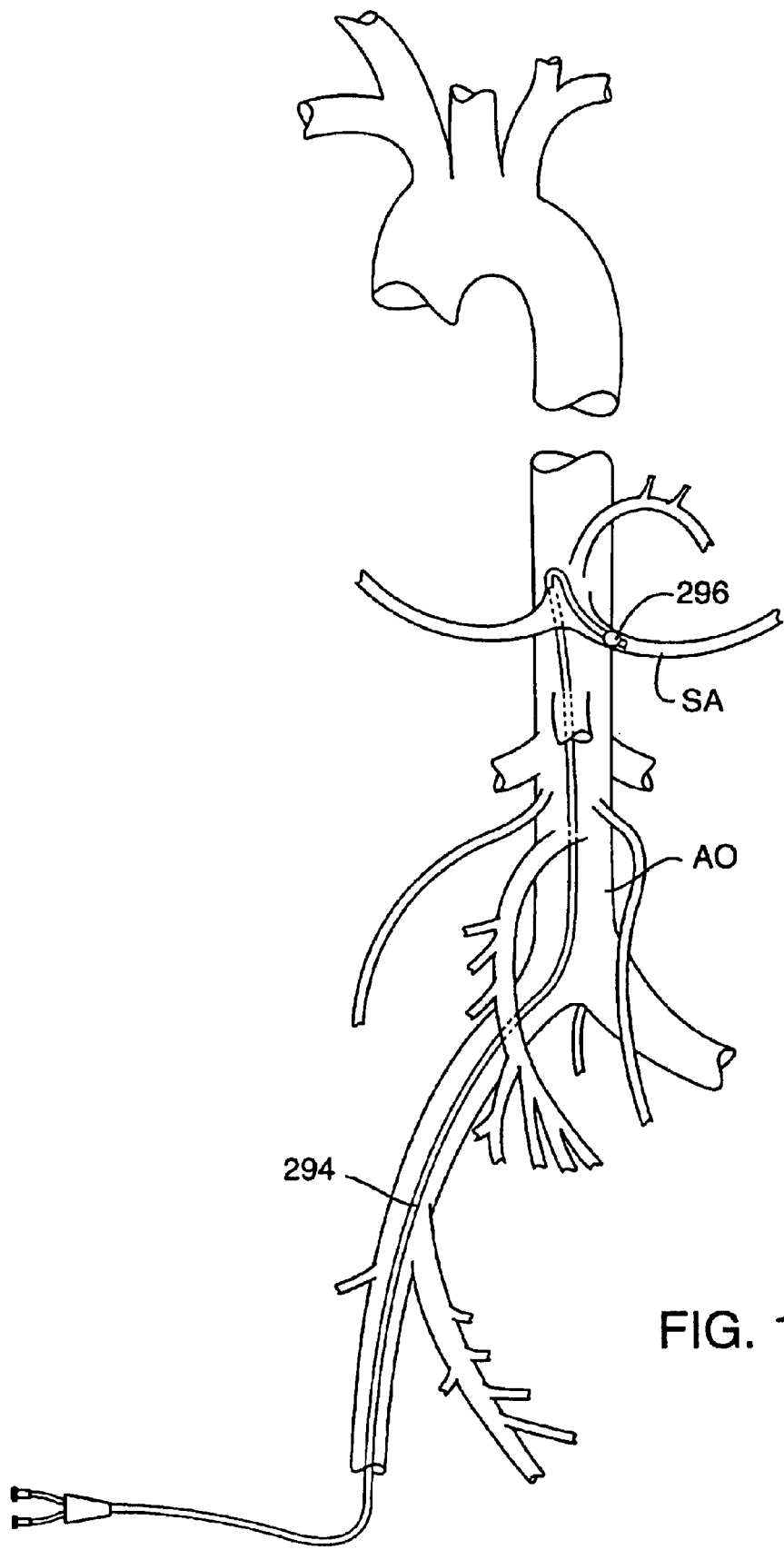
FIG. 11 illustrates the use of a catheter for isolating and perfusing the spleen according to the invention.

Referring to FIG. 11, in order to isolate and perfuse the spleen, a catheter 294 is positioned from the femoral artery through the aorta and celiac trunk into the splenic artery SA, where occlusion balloon 296 may be inflated for arterial occlusion. Venous blood drains from the spleen through the splenic vein, which drains into the portal vein. The portal vein PV is again catheterized and occluded as described above in connection with FIGS. 6A–C. Alternatively, a catheter may be positioned in or around the hepatic veins via the IVC as described above in connection with FIGS. 6B and 6D, although occlusion and collection of the agent in the portal vein is usually preferred to avoid exposure of the liver to the agent.

Figure 12:
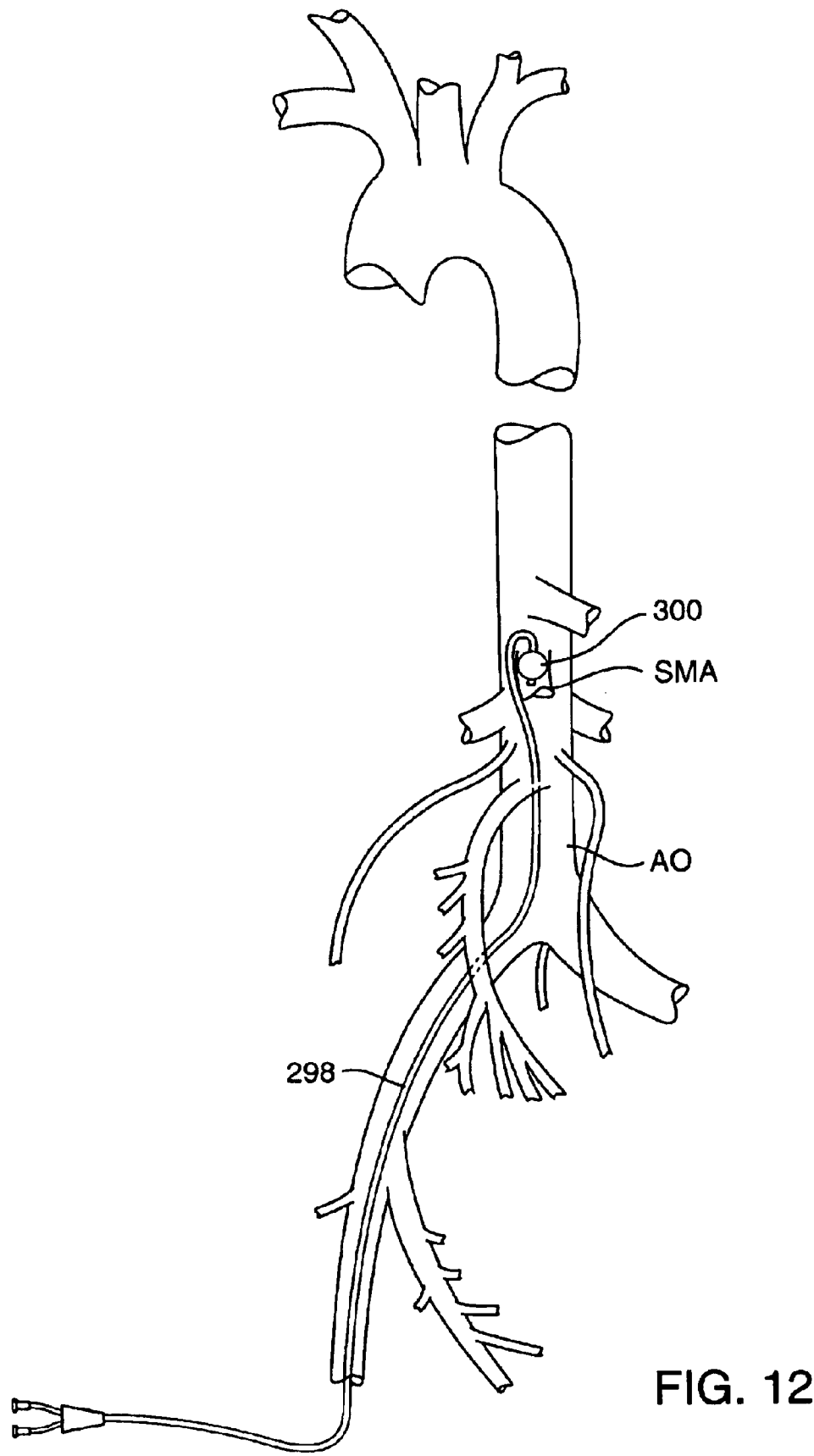
FIG. 12 illustrates the use of a catheter for isolating and perfusing the small bowel according to the invention.
Figure 13:
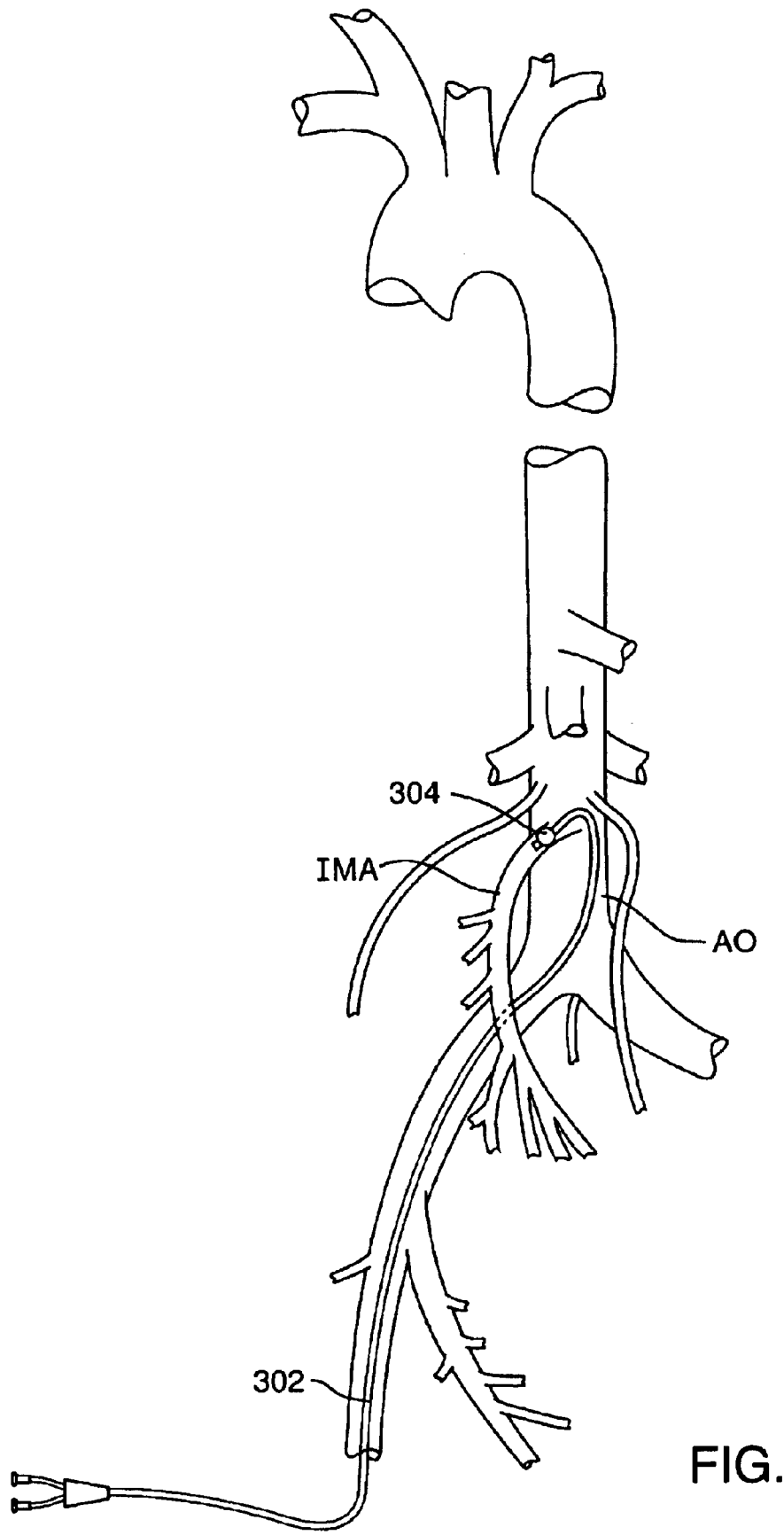
FIG. 13 illustrates the use of a catheter for isolating and perfusing the large intestine according to the invention.

FIGS. 12–13 illustrate methods of isolating and perfusing the small and large bowel. As shown in FIG. 12, a catheter 298 is introduced from the femoral artery through the abdominal aorta into the superior mesenteric artery SMA, and a balloon 300 is inflated to occlude the artery. An agent may then be delivered through catheter 298 to perfuse the small intestine and proximal portion of the colon. For perfusion of the large intestine and distal portion of the colon, as shown in FIG. 13, a catheter 302 is introduced via the femoral artery into the aorta and the inferior mesenteric artery IMA. Balloon 304 is then inflated to occlude the artery, allowing for isolated perfusion of the large intestine and colon. In order to collect the agent and optionally provide recirculation, a balloon occlusion catheter is positioned in the portal vein PV as described above. Alternatively, a catheter may be positioned in or around the hepatic veins via the IVC as described above in connection with FIGS. 6B and 6D, although occlusion and collection of the agent in the portal vein is usually preferred to avoid exposure of the liver to the agent.

Figure 14:
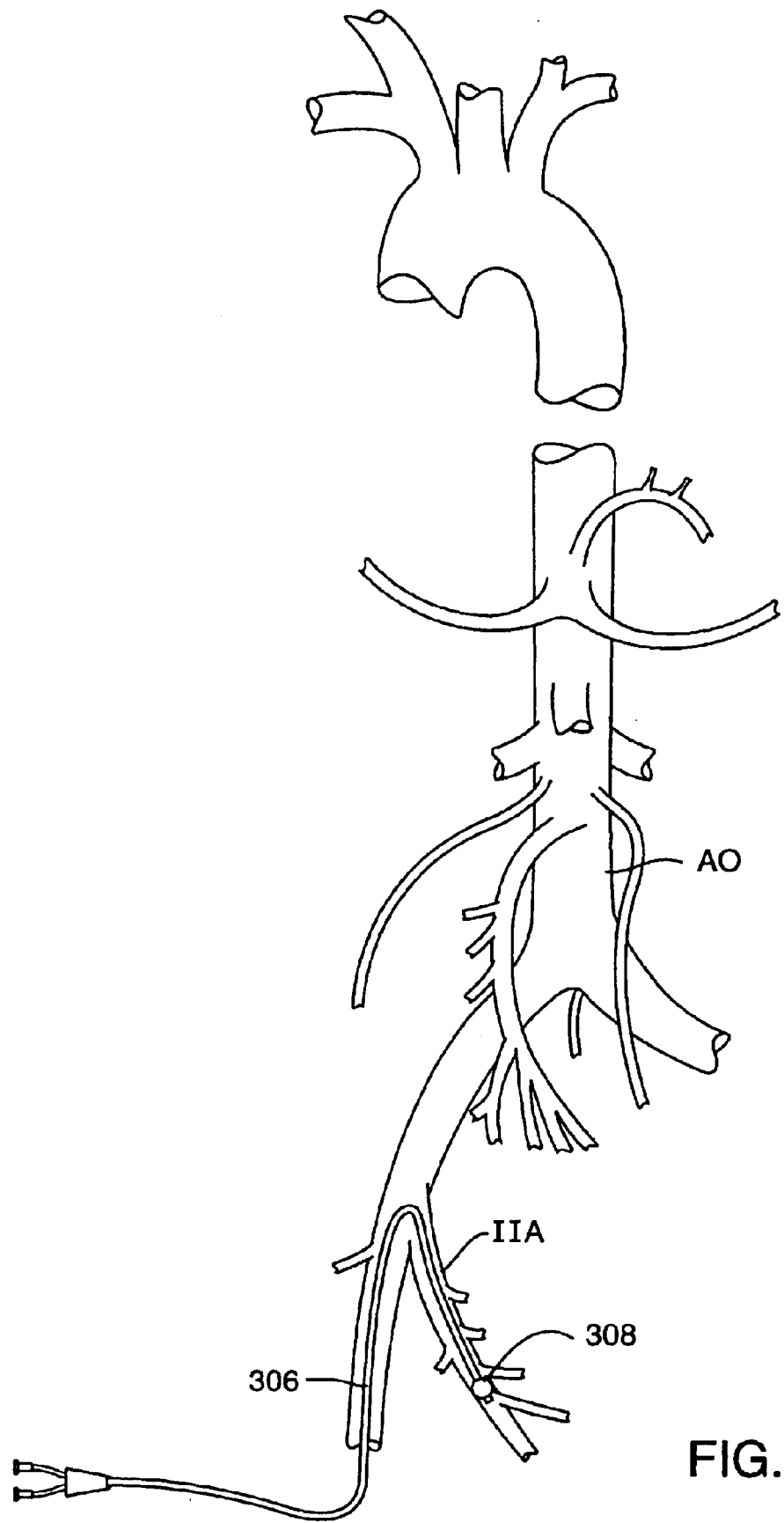
FIG. 14 illustrates the use of a catheter for isolating and perfusing the pelvic organs according to the invention.

In order to perfuse the pelvis, including the bladder, uterus, rectum and some genital regions, a catheter 306 may be positioned as illustrated in FIG. 14, from the femoral artery into the internal iliac artery IIA branching therefrom. Either the anterior or posterior branch of the internal iliac artery may be subselected, depending upon the target tissue structure. Catheter 306 is advanced distally to the desired location of perfusion, and balloon 308 is inflated. Catheter 306 may be configured to occlude the internal iliac artery itself, as illustrated, or to be positioned in the particular artery branching from the internal iliac that supplies the target organ. Alternatively, a double balloon catheter similar to that shown in FIGS. 6D–F may be configured to occlude the internal iliac artery IAA both upstream and downstream from the desired branching artery so as to isolate it from arterial circulation. The agent may be collected on the venous side through an occlusion catheter (not shown) positioned from the femoral vein into the internal iliac vein, or into the particular vein branching from the internal iliac vein which drains the target organ.

Figure 15:
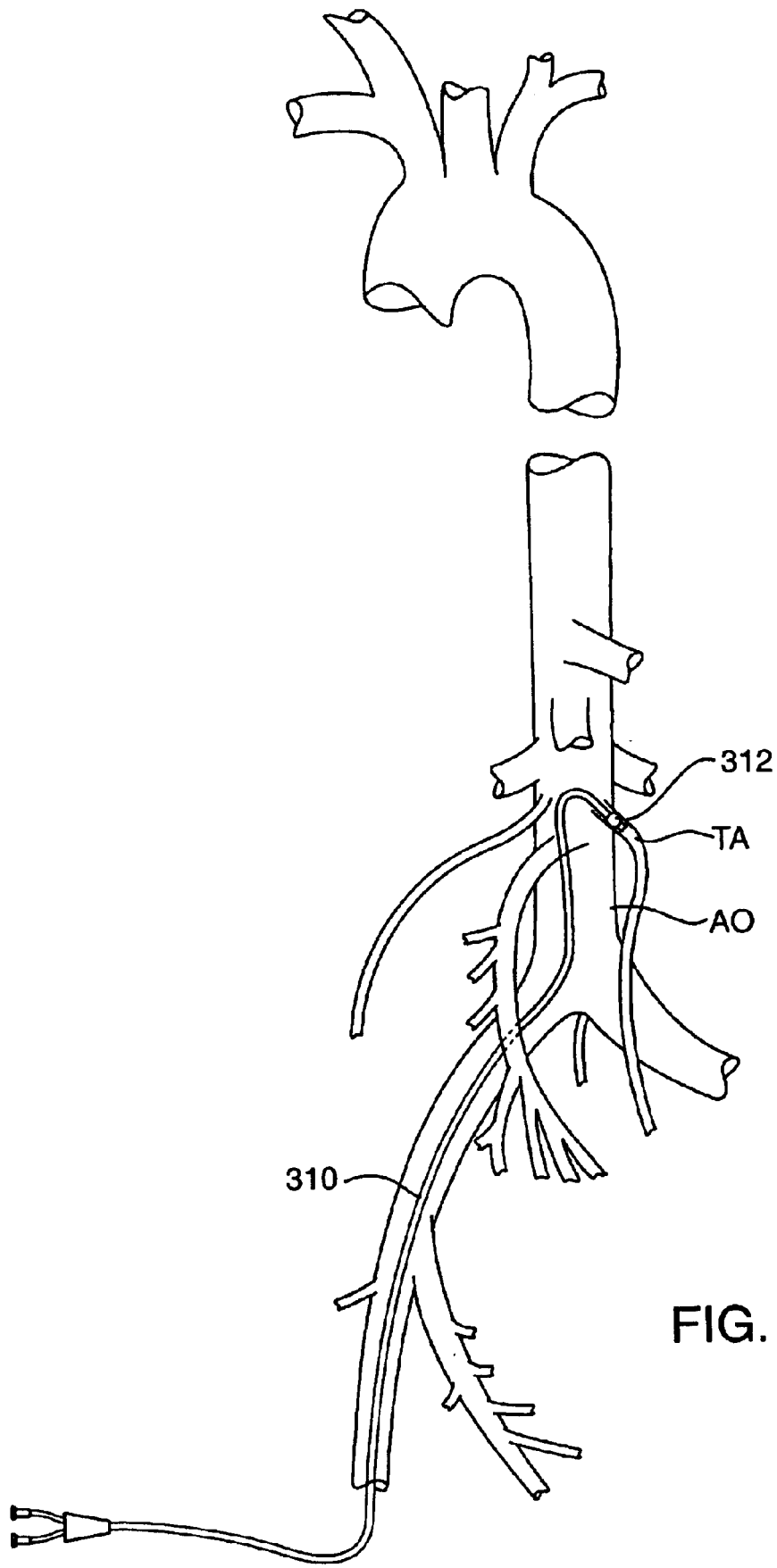
FIG. 15 illustrates the use of a catheter for isolating and perfusing the testicles or ovaries according to the invention.

FIG. 15 illustrates a method of isolating and perfusing the testicles or ovaries. A catheter 310 is advanced from the femoral artery into the abdominal aorta and into the right or left testicular or ovarian arteries TA branching therefrom. Balloon 312 may be inflated to occlude the artery, allowing for isolated perfusion of the testicle or ovary. The perfusate may be collected and/or recirculated through an occlusion catheter positioned in the right or left testicular or ovarian vein via the femoral vein and inferior vena cava (not illustrated).

The methods and apparatus of the invention may also be used for isolation and perfusion of the breast for treatment of cancer and other diseases of the breast. This may be accomplished by occluding the internal mammary artery and the intercostal arteries by placing balloon catheters (not shown) via the femoral artery and aorta into these arteries, and by occluding the intercostal veins by means of a balloon catheter (not shown) placed from the femoral vein or internal jugular vein through the inferior vena cava into the intercostal veins. Isolation of the intercostal arteries may be simplified by placing a double-balloon catheter like that shown in FIGS. 6E–F into the aorta via the femoral artery and positioning one balloon upstream of the intercostal arteries and the other balloon downstream of the intercostal arteries. Each balloon is inflated to isolate the intercostal arteries from the aorta. Blood flow across the isolated region is allowed through the perfusion lumen in the catheter, which will be of sufficient size to provide adequate blood flow through the aorta to sustain the patient during treatment. Therapeutic and other agents may be delivered into or collected from the intercostal arteries through the openings disposed between the two balloons. Similarly, a double-balloon catheter of like construction may be placed in the inferior vena cava via the femoral vein, with occlusion balloons positioned upstream and downstream of the intercostal veins, thus allowing delivery or collection of perfusate from the intercostal veins while blood flow continues through the inferior vena cava. Perfusion of the breast may then be performed either antegrade or retrograde, and either bilaterally or unilaterally.

It should be understood that in any of the foregoing methods of organ isolation and perfusion, both delivery and collection of the therapeutic agent may be accomplished solely through the catheters placed on the arterial side of the organ. For example, following occlusion of the artery(s)

supplying blood to the organ, the therapeutic agent may be delivered into the organ through the arterial catheter(s), allowed to dwell in the organ for a desired time period, then collected by applying suction through the arterial catheter(s). Occlusion of the arteries supplying blood to the organ inhibits the therapeutic agent from being flushed downstream into the venous circulation. Alternatively, retrograde delivery and collection of therapeutic agent may be performed solely through the catheters used to occlude the veins draining blood from the organ. In this way, occlusion catheters must be positioned only on the arterial or venous sides of the organ, thereby simplifying the procedure. However, in most cases, both venous and arterial isolation of the organ will be preferred to allow for total isolation of the organ and for both antegrade and retrograde delivery and collection of agents.

Figure 16:
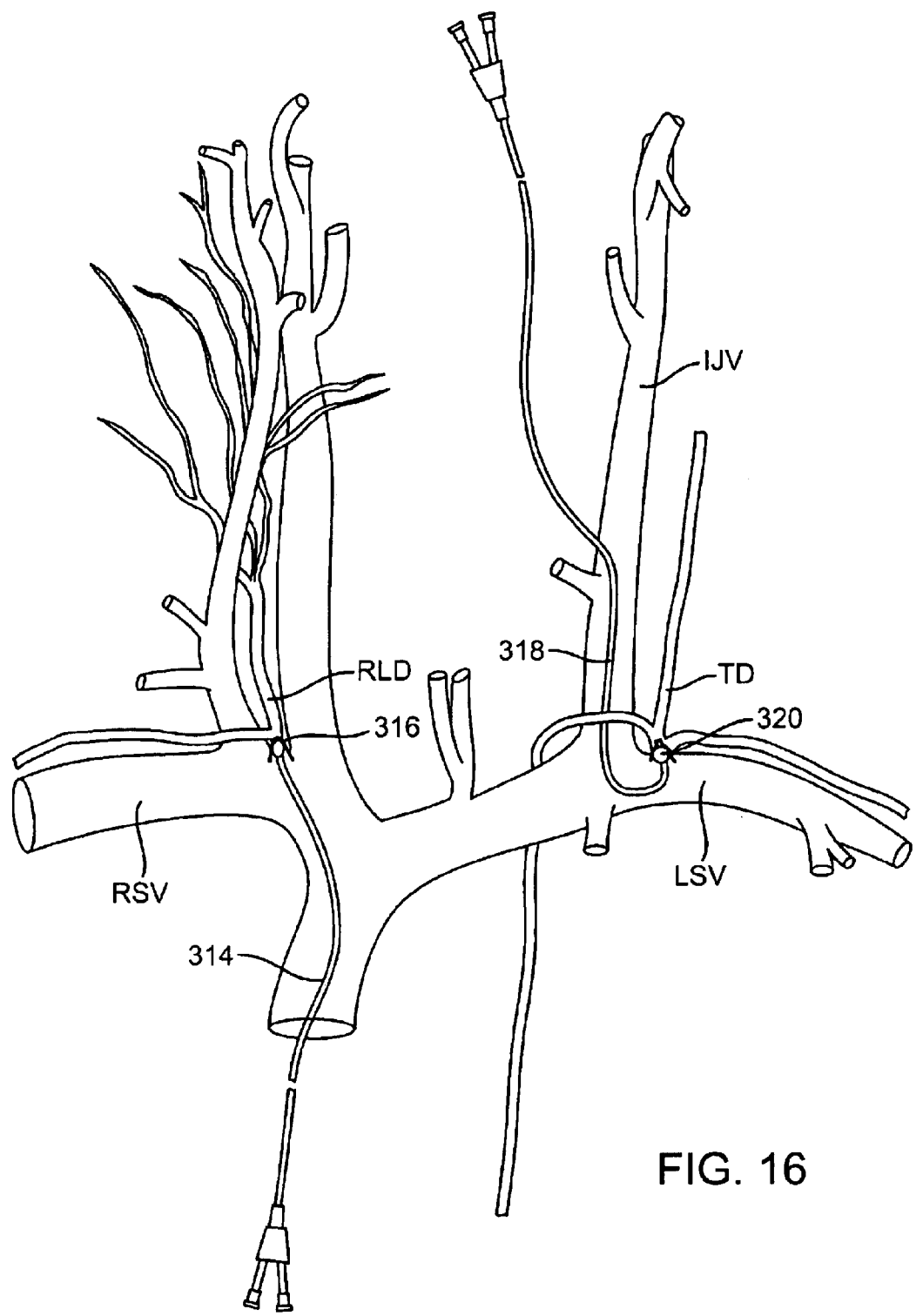
FIG. 16 illustrates the use of catheters for isolating and perfusing the lymphatic ducts according to the invention.

Any of the methods of organ isolation and perfusion described above may be enhanced by the concurrent isolation of regions of the lymph system. This may be accomplished, as shown in FIG. 16, by positioning a catheter 314 from the femoral vein, through the right atrium, superior vena cava, and right subclavian vein RSV into the ostium of the right lymphatic duct RLD. A balloon 316 may then be inflated to occlude the right lymphatic duct RLD, thereby allowing for collection of fluid from or delivery of an agent into the duct. As the right lymphatic duct RLD drains the right jugular lymphatic trunk and the right subclavian lymphatic trunk from the right side of the head, neck and trunk, this technique may be particularly useful in conjunction with perfusion of the brain or lungs. Additionally or alternatively, a catheter 318 may be introduced via the left internal jugular vein IJV or through the femoral vein as with catheter 314 described above, into the left subclavian vein LSV and into the ostium of the thoracic duct TD, which drains most of the tissues of the body not drained by the right lymphatic duct. A balloon 320 is then inflated to occlude the thoracic duct TD, permitting infusion or collection of agents to or from the lymph system. Lymphatic pressure may be altered. Lymphatic fluid may also be drained from the system, filtered and returned or replaced. Such isolation of the thoracic duct may be particularly beneficial in conjunction with isolation and perfusion of the brain as well as the heart, lungs, liver, kidneys, stomach, spleen, bowel, colon, testicles, ovaries and pelvic organs.

Figure 17:
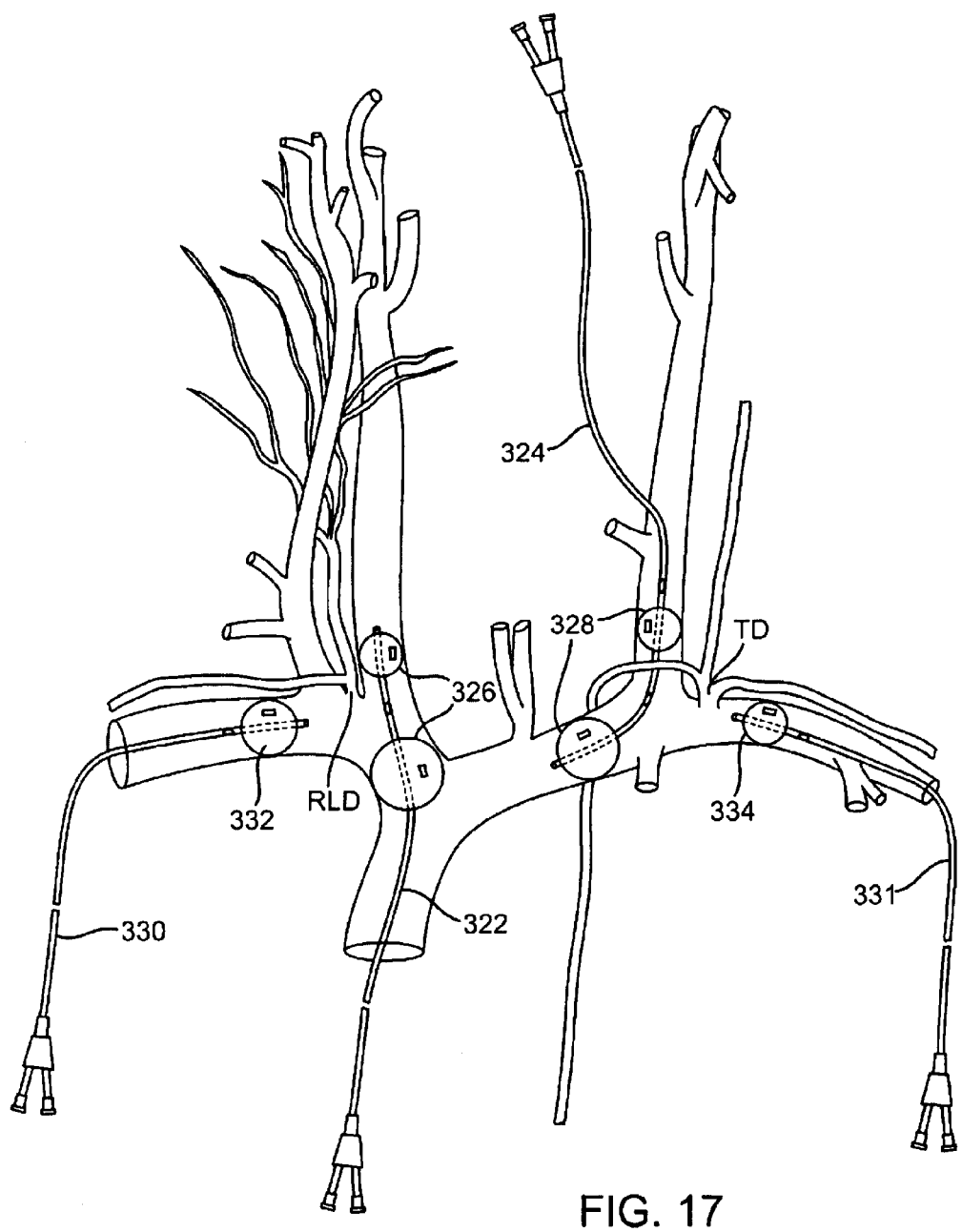
FIG. 17 illustrates the use of double balloon catheter and a single balloon catheter in an alternative method of isolating and perfusing the lymphatic ducts according to the invention.

An alternative technique of isolating the lymphatic ducts is illustrated in FIG. 17. In this method, double balloon occlusion catheters 322, 324 are introduced via the femoral vein (as illustrated with the right lymphatic duct RLD) or via the internal jugular vein IJV (as illustrated with the thoracic duct TD). A pair of balloons 326, 328 on each catheter is inflated on either side of the branching subclavian veins RSV, LSV. An additional catheter 330,331 is introduced into the subclavian vein and a balloon 332, 334 is inflated in the subclavian vein distally of the ostium of the lymphatic duct which drains into such vein. In this way, isolation of the lymphatic ducts may be accomplished without catheterization of the ducts themselves. Perfusate may then be either delivered or collected via openings in catheters 322, 324 between each pair of balloons. If desired, a perfusion lumen may be provided in each catheter to allow for blood flow across the isolated region of the jugular veins, in a manner similar to catheter 260 illustrated in FIGS. 6D–E.

Various means of visualization may be used to facilitate placement of the catheters described herein. The catheters may incorporate radio-opaque materials or markers to enhance visualization using fluoroscopy. Radio-opaque dyes may be injected in the desired region prior to placement or through the catheters themselves during placement to identify the target vessels. Ultrasonic reflectors or emitters may be mounted on the catheters for visualization via ultrasound. Magnetic resonance imaging may also be utilized.

While being particularly effective for perfusion of isolated organs and other tissue structures, the methods and apparatus of the invention may also utilized for perfusion of a major portion of an organism while a particular organ, series of organs or tissue region is isolated from such perfusion. For example, for the treatment of diseases of the musculoskeletal system, it may be advantageous to perfuse all or major portions of the body with therapeutic agents while isolating certain organs such as the kidneys and liver from such agents. The catheters and methods described above may be used to accomplish such isolation, with perfusion of the remainder of the organism being performed through the same or different catheters.

Figure 18:
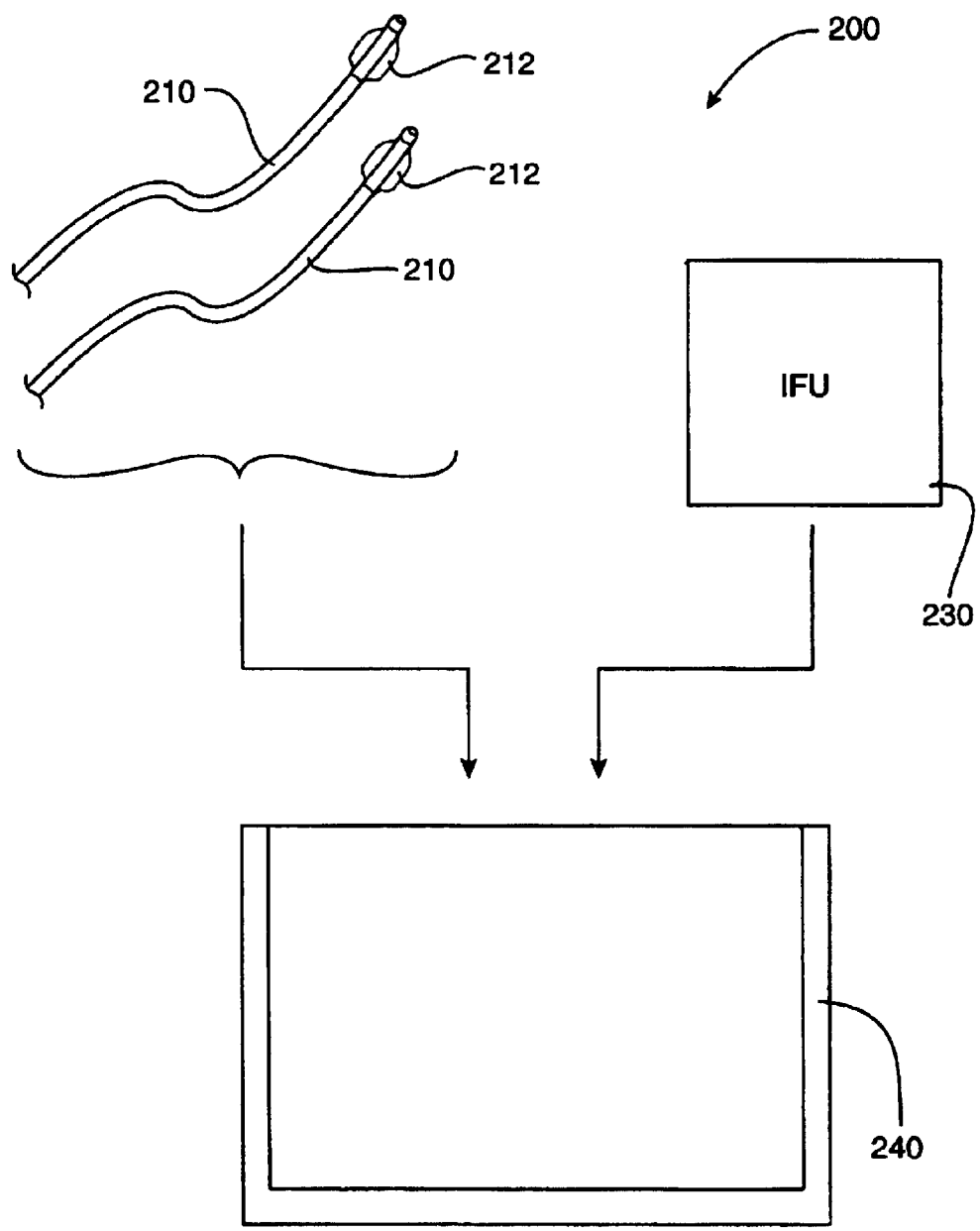
FIG. 18 is a schematic illustration of a kit comprising catheters, instructions for use, and a package, according to the present invention.

Referring now to FIG. 18, kits 200 according to the present invention will comprise a catheter set, preferably including at least one catheter, usually at least two catheters, having dimensions, flexibility characteristics, access lumens, and occluding members which are selected for blocking blood or other fluid flow to and from particular organs or other tissue structures as described above. The catheters themselves may be of relatively simple construction, usually comprising a catheter body 210 having at least one lumen therethrough and at least one inflatable balloon 212 near a distal end of the catheter body for occluding the target blood vessel. The catheters in the catheter set will usually not be identical and will have characteristics selected for the particular target blood vessel. The catheter sets may include as few as two catheters for isolating and perfusing the kidney, prostate, bowel, colon, spleen, stomach, testicles, ovaries, and certain other organs as described above. The catheter set may also include as many as eight or more catheters for total isolation and perfusion of the brain and other region of the body.

In addition to the catheters 210, the kits 200 will usually also include instructions for use 230 setting forth any of the methods described above. The instructions for use will usually be printed on a package insert, but may also be printed on a portion of the packaging. The instructions for use may further include instructions as to the particular types of pharmaceuticals to be administered, dosages, frequencies of administration, and other information concerning the agents to be delivered using the catheters described herein. In some cases, these instructions for use may instruct the user to administer certain types of drugs, or certain concentrations, dosage levels, frequencies of administration, temperatures, pressures, or other delivery parameters of such drugs, which provide the maximum therapeutic effect when used with the catheters and methods described herein, but which might even be toxic or cause serious injury if delivered systemically using conventional devices and methods.

The kits 200 will usually still further comprise a package 240 for containing the catheters 210 and/or instructions for use 230. The package 240 may take any conventional form, e.g. a pouch, box, tray, tube, or the like.

The kits may comprise other components such as tubing, filters, heaters, coolers, oxygenators, and other components of the extracorporeal blood/oxygenated medium circulation system. In addition, the kits may comprise the therapeutic and/or diagnostic agents to be delivered using the kit. Exemplary agents have been described above, any of which may be included in the kit.

The catheters 210 and other components of the kit will usually be sterilized within the package 240 using conventional sterilization techniques. Most commonly, the sterilization will be done using a sterilant gas, such as ethyleneoxide, or by radiation after the package has been sealed.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of treatment of a tissue structure in a patient, the tissue structure being coupled to an artery through which blood flows from the patient's circulatory system to the tissue structure and to a vein through which blood flows away from the tissue structure to the circulatory system, the method comprising:

endovascularly positioning a first catheter in the artery;

endovascularly positioning a second catheter in the vein;

occluding the artery around the first catheter;

occluding the vein around the second catheter;

delivering a perfusate comprising a therapeutic agent and an oxygen carrier to the tissue structure through at least one of the first and second catheters while the artery and vein remain occluded, the tissue structure being an organ selected from the group consisting of the brain, at least one breast, at least one lung, at least one kidney, the liver, the spleen, the stomach, the intestines, the pancreas, the colon, the bladder, the thyroid gland, and the prostate;

collecting the perfusate through the other of the at least one of the first and second catheters after the perfusate has perfused at least a portion of the tissue structure;

extracorporeally pumping the perfusate back to the at least one of the first and second catheters; and extracorporeally oxygenating the oxygen carrier.

2. The method as in claim 1, wherein the perfusate is delivered through the first catheter into the artery and collected from the vein by the second catheter to establish antegrade perfusion.

3. The method as in claim 1, wherein the perfusate is delivered through the second catheter into the vein and collected from the artery by the first catheter to establish retrograde perfusion.

4. A method as in claim 1, wherein the perfusate comprises an agent selected from the group consisting of a drug, a diagnostic agent, and a biologic material.

5. The method as in claim 1, wherein the oxygenated carrier is a synthetic oxygen carrier.

6. The method as in claim 1, wherein the oxygenated carrier is oxygenated blood.

7. The method of claim 1, comprising the step of heating the tissue structure during the delivering step.

8. The method of claim 7, wherein the heating step raises the temperature of the tissue structure to at least about 100° F.

9. The method of claim 7, wherein the heating step raises the temperature of the tissue structure to at least about 105° F.

10. The method of claim 7, wherein the heating step comprises heating the perfusate before the delivering step, and wherein the perfusate transfers heat to the tissue structure.

11. A method of treatment of a tissue structure in a patient, the tissue structure being coupled to an artery through which blood flows from the patient's circulatory system to the tissue structure and to a vein through which blood flows away from the tissue structure to the circulatory system, the method comprising:

endovascularly positioning a first catheter in the artery;

endovascularly positioning a second catheter in the vein;

occluding the artery around the first catheter; and occluding the vein around the second catheter; and delivering a perfusate to the tissue structure through at least one of the first and second catheters while the artery and vein remain occluded, wherein the tissue structure is a liver, the first catheter occludes a hepatic artery, the second catheter occludes a hepatic vein, and a third catheter occludes a portal vein.

12. The method as in claim 11, further comprising adding therapeutic agent to the perfusate.

13. The method as in claim 11, wherein the perfusate is delivered through at least one of the first and third catheters and collected in the second catheter to establish antegrade perfusion.

14. The method as in claim 11, wherein the perfusate is delivered through the second catheter and collected in at least one of the first and third catheters to establish retrograde perfusion.

15. The method of claim 11, comprising the step of heating the tissue structure during the delivering step.

16. The method of claim 15, wherein the heating step raises the temperature of the tissue structure to at least about 100° F.

17. The method of claim 15, wherein the heating step raises the temperature of the tissue structure to at least about 105° F.

18. The method of claim 15, wherein the heating step comprises heating the perfusate before the delivering step, and wherein the perfusate transfers heat to the tissue structure.

* * * * *